United States Patent
Andersen

(10) Patent No.: US 11,357,414 B2
(45) Date of Patent: Jun. 14, 2022

(54) METHODS, SYSTEMS AND DEVICES THAT USE CONDUCTIVE COMMUNICATION TO DETERMINE TIME DELAY FOR USE IN MONITORING BLOOD PRESSURE

(71) Applicant: Pacesetter, Inc., Sylmar, CA (US)

(72) Inventor: Dean P. Andersen, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 578 days.

(21) Appl. No.: 16/396,408

(22) Filed: Apr. 26, 2019

(65) Prior Publication Data

US 2020/0337563 A1 Oct. 29, 2020

(51) Int. Cl.
| | |
|---|---|
| *A61B 5/0215* | (2006.01) |
| *A61B 5/024* | (2006.01) |
| *A61N 1/365* | (2006.01) |
| *A61B 5/00* | (2006.01) |
| *A61N 1/37* | (2006.01) |

(Continued)

(52) U.S. Cl.
CPC .......... *A61B 5/0215* (2013.01); *A61B 5/0028* (2013.01); *A61B 5/0031* (2013.01); *A61B 5/0295* (2013.01); *A61B 5/02416* (2013.01); *A61B 5/686* (2013.01); *A61N 1/05* (2013.01); *A61N 1/36564* (2013.01); *A61N 1/3706* (2013.01); *A61N 1/37512* (2017.08); *A61B 5/02125* (2013.01); *A61B 5/0535* (2013.01);

(Continued)

(58) Field of Classification Search
CPC .......................... A61B 5/0028; A61B 5/02125
See application file for complete search history.

(56) References Cited

U.S. PATENT DOCUMENTS

| 9,687,656 B2 | 6/2017 | Wenzel et al. |
| 2010/0185055 A1* | 7/2010 | Robertson ............ A61B 5/0073 600/117 |

(Continued)

OTHER PUBLICATIONS

L. Peters, N. Nouryb, and M. Cerny, "Review of methods for non-invasive and continuous blood pressure monitoring Pulse transit time method is promising." Innovation Res. BioMed Eng., vol. 35, No. 5, pp. 271-282, 2014.

(Continued)

*Primary Examiner* — Meredith Weare
(74) *Attorney, Agent, or Firm* — Vierra Magen Marcus LLP

(57) ABSTRACT

A system for monitoring blood pressure includes an implantable medical device (IMD) and an external device (ED). The IMD senses an electrogram (EGM) signal, identifies a feature thereof indicative of a ventricular depolarization, and transmits a conductive communication signal through patient tissue indicating when the ventricular depolarization occurred. The ED is worn against skin and configured to receive the conductive communication signal. The ED is also configured to sense a plethysmography (PG) signal and identify a feature thereof indicative of when a pulse wave responsive to the ventricular depolarization reaches a region of the patient adjacent the ED, and determine a delay time (TD) indicative of how long it takes the pulse wave to travel from the patient's heart to the region of the patient adjacent to the ED. The TD is a surrogate of the patient's blood pressure and useful for monitoring the patient's blood pressure and/or changes therein.

26 Claims, 10 Drawing Sheets

(51) Int. Cl.
  *A61B 5/0295* (2006.01)
  *A61N 1/375* (2006.01)
  *A61N 1/05* (2006.01)
  *A61B 5/0535* (2021.01)
  *A61B 5/021* (2006.01)

(52) U.S. Cl.
  CPC ............ *A61B 5/6802* (2013.01); *A61B 5/7278* (2013.01); *A61N 1/36585* (2013.01)

(56) References Cited

U.S. PATENT DOCUMENTS

| | | | |
|---|---|---|---|
| 2012/0197350 A1* | 8/2012 | Roberts | A61N 1/37205 607/60 |
| 2016/0121127 A1* | 5/2016 | Klimovitch | H04W 56/001 607/32 |
| 2016/0277097 A1* | 9/2016 | Ludwig | H04B 13/005 |
| 2016/0317816 A1* | 11/2016 | Winter | A61N 1/37247 |
| 2018/0055386 A1* | 3/2018 | Zielinski | A61B 5/746 |
| 2018/0184921 A1 | 7/2018 | Baxi et al. | |
| 2019/0030230 A1 | 1/2019 | Connor | |
| 2019/0160291 A1* | 5/2019 | Peichel | A61N 1/3975 |
| 2019/0254524 A1* | 8/2019 | Granqvist | A61B 5/0024 |

OTHER PUBLICATIONS

S. Gabriel, R. W. Lau, and C. Gabriel, "The dielectric properties of biological tissues: I. Literature survey" Phys Med. Bio., vol. 41, No. 11, pp. 2231-2249, 1996.

D. Buxi, J. M. Redout and Y. R. Yuce "A survey on signals and systems in ambulatory blood pressure monitoring using pulse transit time," Inst. Phys. Eng. Med. Physiol. Meas., vol. 36, pp. R1-R26, 2015.

G. Lopez et al., "Continuous blood pressure measurement in daily activities," Sensors, 2009 IEEE, Christchurch, 2009, pp. 827-831.

Wegmüller, Marc Simon. "Intra-body communication for biomedical sensor networks." (2007).

Sharma et al., "Cuff-Less and Continuous Blood Pressure Monitoring: A Methodological Review," technologies, MDPI Journal, May 9, 2017, pp. 1-22.

Liu, Shing-Hong, et al., "A Cuffless Blood Pressure Measurement Based on the Impedance Plethysmography Technique," sensors, MDPI Journal, May 21, 2017, pp. 1-13.

* cited by examiner

METHODS, SYSTEMS AND DEVICES THAT USE CONDUCTIVE COMMUNICATION TO DETERMINE TIME DELAY FOR USE IN MONITORING BLOOD PRESSURE

FIELD OF TECHNOLOGY

Embodiments described herein generally relate to methods, systems and devices that can be used to chronically monitor a patient's blood pressure, and more specifically, to methods, systems and devices that determine a time delay (TD) using an implanted medical device (IMD) and an external device (ED), wherein the TD is useful for monitoring the patient's blood pressure and/or changes therein.

BACKGROUND

A person's circulatory system includes both systemic and pulmonary circulation systems. Pulmonary circulation supplies the lungs with blood flow, while the systemic circulation takes care of all the other parts of the body, i.e. the systemic circulation. The heart serves as a pump that keeps up the circulation of the blood. Both the pulmonary and systemic circulatory systems are made up of arteries, arterioles, capillaries, venules and veins. The arteries take the blood from the heart, while the veins return the blood to the heart Blood pressure is defined as the force exerted by the blood against any unit area of the vessel wall. The measurement unit of blood pressure is millimeters of mercury (mmHg). Pulmonary and systemic arterial pressures are pulsatile, having systolic and diastolic pressure values. The highest recorded pressure reading is called systolic pressure, which results from the active contraction of the ventricle. Although the arterial pressure and indeed flow in the arteries is pulsatile, the total volume of blood in the circulation remains constant. The lowest pressure reading is called diastolic pressure which is maintained by the resistance created by the smaller blood vessels still on the arterial side of the circulatory system (arterioles). Stated another way, the systolic pressure is defined as the peak pressure in the arteries, which occurs near the beginning of a cardiac cycle. In contrast, the diastolic pressure is the lowest pressure, which occurs at the resting phase of the cardiac cycle. The pulse pressure reflects the difference between the maximum and minimum pressures measured (i.e., the difference between the systolic pressure and diastolic pressure). The mean arterial pressure is the average pressure throughout the cardiac cycle.

Arterial pulse pressure, such as mean arterial pressure (MAP), is a fundamental clinical parameter used in the assessment of hemodynamic status of a patient. Mean arterial pressure can be estimated from real pressure data in a variety of ways. Among the techniques that have been proposed, two are presented below. In these formulas, SP is the systolic blood pressure, and DP is diastolic pressure.

$$MAP_2 = (SP+2DF)/3 = \tfrac{1}{3}(SP) + \tfrac{2}{3}(DP),$$

or $$MAP_1 = (SP+DP)/2$$

Systolic pressure and diastolic pressure can be obtained in a number of ways. A common approach is to use a stethoscope, an occlusive cuff, and a pressure manometer. However, such an approach is slow, requires the intervention of a skilled clinician and does not provide timely readings as it is a measurement at only a single point in time. While systolic pressure and diastolic pressure can also be obtained in more automated fashions, it is not always practical to obtain measures of pressure using a cuff and pressure transducer combination, especially if the intention or desire is to monitor arterial pressure on a chronic basis. Arterial pressure is also referred to herein more generally as blood pressure.

Another approach for obtaining measures of arterial pressure is to use an intravascular pressure transducer. However, an intravascular device may cause problems, such as, embolization, nerve damage, infection, bleeding and/or vessel wall damage. Additionally, the implantation of an intravascular lead requires a highly skilled physician such as a surgeon, electrophysiologist, or interventional cardiologist.

Plethysmography, the measurement of volume of an organ or body part, has a history that extends over 100 years. Photoplethysmography (PPG) uses optical techniques to perform volume measurements, and was first described in the 1930s. While best known for their role in pulse oximetry, PPG sensors have also been used to indirectly measure blood pressure. For example, non-invasive PPG sensors have been used in combination with in an inflatable cuff in a device known as Finapres. U.S. Pat. No. 4,406,289 (Wesseling et al.) and U.S. Pat. No. 4,475,940 (Hyndman) are exemplary patents that relate to the Finapres technique. The cuff is applied to a patient's finger, and the PPG sensor measures the absorption at a wavelength specific for hemoglobin. After the cuff is used to measure the individual's mean arterial pressure, the cuff pressure around the finger is then varied to maintain the transmural pressure at zero as determined by the PPG sensor. The Finapres device tracks the intra-arterial pressure wave by adjusting the cuff pressure to maintain the optical absorption constant at all times.

There are a number of disadvantages to the Finapres technique. For example, when there exists peripheral vasoconstriction, poor vascular circulation, or other factors, the blood pressure measured in a finger is not necessarily representative of central blood pressure. Further, maintaining continuous cuff pressure causes restriction of the circulation in the finger being used, which is uncomfortable when maintained for extended periods of time. Accordingly, the Finapres technique is not practical for continuous monitoring of blood pressure.

In the past few years, research groups have worked on developing cuff-less blood pressure monitoring systems, which hope to provide continuous monitoring of a patient's blood pressure without interruption to their daily activities. The underlying principle of these system is based on the relation of the time (also known as time delay) it takes for a volume of blood (in the form of a pulse) to travel from the heart to a peripheral region, which could be in the form of pulse transit time (PTT) or pulse arrival time (PAT). Algorithms and mathematical models have been proposed to convert measures of PTT and/or PAT to measures of blood pressure. The "time delay" is usually obtained by measuring a time between an R-wave of electrocardiogram (ECG) obtained using surface electrodes, and a feature of a photoplethysmography (PPG) signal obtained using a finger or earlobe worn pulse oximeter. However, existing systems typically use ECG acquisition approaches that require a cross-body configuration, requiring the user to be in contact with electrode(s) on the wearable device, hence not providing for continuous monitoring of blood pressure.

As is evident from the above description, there is the need for improved systems and methods for monitoring arterial blood pressure on a chronic bases.

SUMMARY

Certain embodiments of the present technology relate to methods for use in monitoring a patient's blood pressure. Such a method can include an implantable medical device (IMD) sensing an electrogram (EGM) signal indicative of cardiac electrical activity of the patient's heart, the IMD identifying a feature of the EGM signal indicative of a ventricular depolarization of the patient's heart, and the IMD transmitting a conductive communication signal through patient tissue using at least two implanted electrodes of the IMD, wherein the conductive communication signal indicates when the ventricular depolarization of the patient's heart occurred. Such a method can further includes an external device (ED), worn against skin of the patient, receiving the conductive communication signal using at least two electrodes of the ED that are in contact with skin of the patient against which the ED is worn. Additionally, the method can include the ED sensing a plethysmography (PG) signal indicative of variations in blood volume in a region of the patient adjacent to the ED. The method can also include the ED identifying a feature of the PG signal indicative of when a pulse wave responsive to the ventricular depolarization reaches the region of the patient adjacent to the ED, and the ED determining a time delay (TD) based on the conductive communication signal received by the ED from the IMD, and based on the feature of the PG signal identified by the ED. In such embodiments the TD, which is indicative of how long it takes the pulse wave to travel from the patient's heart to the region of the patient adjacent to the ED, is a surrogate of the patient's blood pressure and can be used to monitor the patient's blood pressure and/or changes therein. The method can also include the ED monitoring the patient's blood pressure and/or changes therein based on the TD. The ED can be a wrist worn device that resemble a watch in certain embodiments, but that need not be the case in other embodiments.

In accordance with certain embodiments, the IMD comprises a leadless pacemaker (LP) that is implanted in or on a cardiac chamber of the patient's heart. In alternative embodiments, the IMD can be a pacemaker and/or ICD that includes a housing implanted in a pectoral region with leads having electrodes implanted within a patient's heart. The IMD can alternatively be a monitoring device that provides no therapy. Other variations are also possible and within the scope of the embodiments described herein.

In accordance with certain embodiments, the method further includes the IMD increasing, from time to time, an amplitude of a conductive communication signal indicating when a ventricular depolarization of the patient's heart occurred, to thereby increase a probability that the ED can detect the conductive communication signal and used that it learns therefrom to monitors that patient's blood pressure and/or changes therein.

In accordance with certain embodiments, a same two implanted electrodes of the IMD that are used to perform the sensing the EGM are also used to perform the transmitting the conductive communication signal through patient tissue. In alternative embodiments, that need not be the case.

In accordance with certain embodiments, the IMD transmits the conductive communication signal through patient tissue, using at least two implanted electrodes of the IMD, during a refractory period that follows the ventricular depolarization of the patient's heart.

In accordance with certain embodiments, the PG signal comprises a photoplethysmography (PPG) signal and a sensor of the ED that senses the PPG signal comprises an optical sensor that includes at least one light emitting element and at least one light detecting element. Alternatively, the PG signal can comprise an impedance plethysmography (IPG) signal and a sensor of the ED that senses the IPG signal comprises at least two electrodes. In certain embodiments, a same two electrodes of the ED that are used to receive the conductive communication signal are also used to sense the IPG signal, however that need not be the case in other embodiments.

Certain embodiments of the present technology are directed to a system for use in monitoring a patient's blood pressure. Such a system can include an implantable medical device (IMD) comprising a plurality of implantable electrodes, and an external device (ED) comprising a plurality of external electrodes. The IMD is configured to sense an electrogram (EGM) signal using at least two of the plurality of implantable electrodes of the IMD, the EGM signal indicative of cardiac electrical activity of the patient's heart. Additionally, the IMD is configured to identify a feature of the EGM signal indicative of a ventricular depolarization of the patient's heart, and transmit a conductive communication signal through patient tissue using at least two of the plurality of implantable electrodes of the IMD, the conductive communication signal indicating when the ventricular depolarization of the patient's heart occurred. The ED is configured to be worn against skin of a patient such that the external electrodes are in contact with the skin of the patient. In certain embodiments, the ED is a wrist worn device, but that need not be the case in other embodiments. The ED is configured to receive the conductive communication signal, using at least two of the external electrodes of the ED that are in contact with skin of the patient against which the ED is worn. Further, the ED is configured to sense a plethysmography (PG) signal indicative of variations in blood volume in a region of the patient adjacent to the ED, and identify a feature of the PG signal indicative of when a pulse wave responsive to the ventricular depolarization reaches the region of the patient adjacent to the ED. The ED is also configured to determine a delay time (TD) based on the conductive communication signal received by the ED from the IMD, and based on the feature of the PG signal identified by the ED. The TD, which is indicative of how long it takes the pulse wave to travel from the patient's heart to the region of the patient adjacent to the ED, is a surrogate of the patient's blood pressure and can be used to monitor the patient's blood pressure and/or changes therein. The ED can further be configured to monitor the patient's blood pressure and/or changes therein based on the TD.

In accordance with certain embodiments, the IMD is configured increase, from time to time, an amplitude of a conductive communication signal indicating when a ventricular depolarization of the patient's heart occurred, to thereby increase a probability that the ED can detect the conductive communication signal.

In accordance with certain embodiments, a same two implantable electrodes of the IMD that are used to sense the EGM are also used to transmit the conductive communication signal, receivable by the ED, through patient tissue.

In accordance with certain embodiments, the IMD is configured to transmit the conductive communication signal through patient tissue, using the at least two of the plurality of implantable electrodes of the IMD, indicating when the ventricular depolarization of the patient's heart occurred, during a refractory period that follows the ventricular depolarization of the patient's heart.

Certain embodiments of the present technology are directed to a device configured to be worn on a patient's body, wherein the device includes a plurality of electrodes, a receiver coupled to the electrodes, a sensor, and one or more processors. The plurality of electrodes are configured to be in contact with skin of the patient wearing the device. The receiver is configured to receive a conductive communication signal, using at least two of the electrodes that are in contact with skin of the patient against wearing the device. The sensor is configured to sense a plethysmography (PG) signal indicative of variations in blood volume in a region of the patient adjacent to the device. The processor(s) is/are configured to identify a feature of the PG signal indicative of when a pulse wave responsive to the ventricular depolarization reaches the region of the patient adjacent to the device, and determine a delay time (TD) based on the conductive communication signal received by the device from the IMD, and based on the feature of the PG signal identified by the device, wherein the TD is indicative of how long it takes a pulse wave to travel from the patient's heart to the region of the patient adjacent to the device. The processor(s) is/are also configured to monitor the patient's blood pressure, and/or changes therein, based on the TD.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1A:
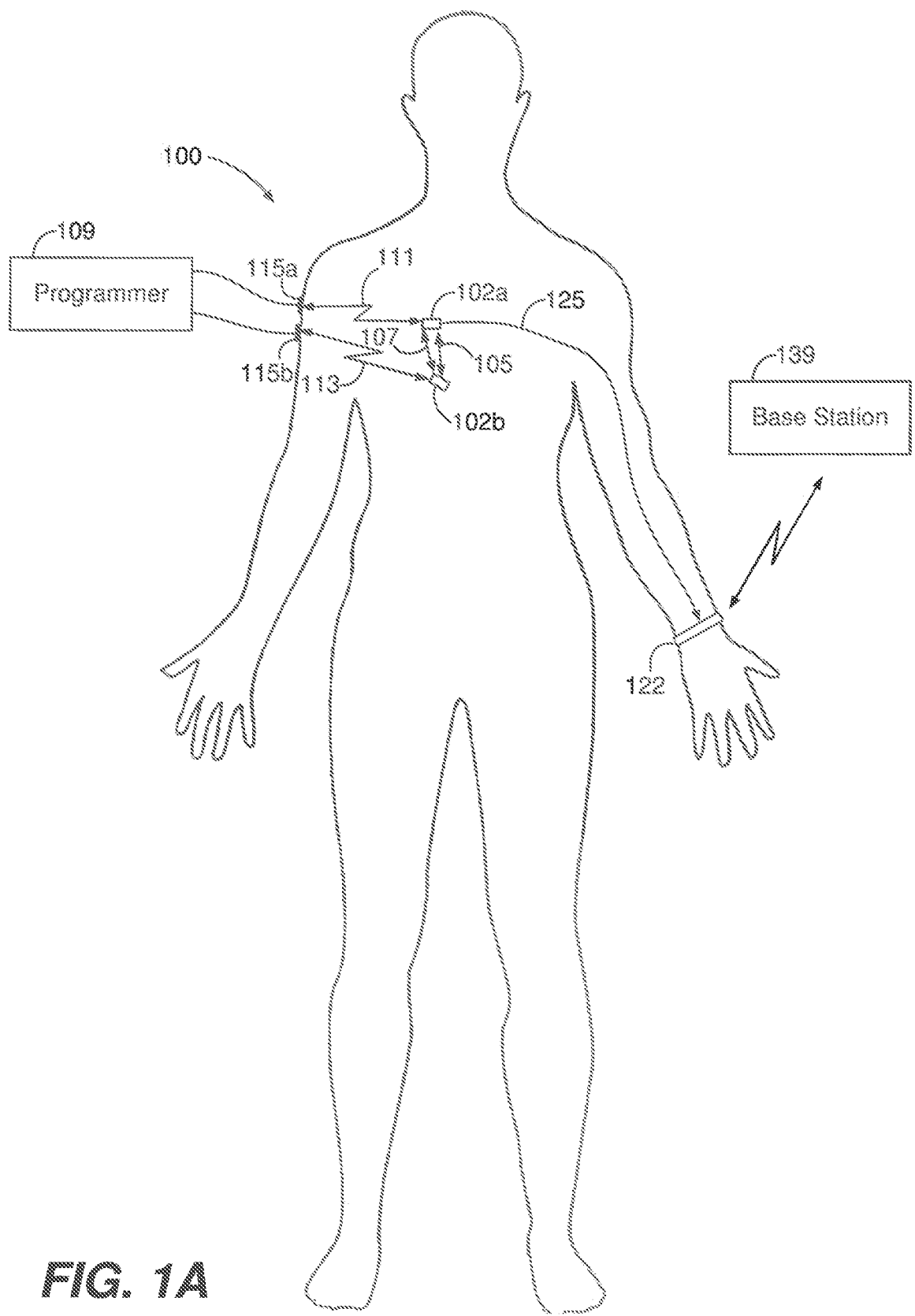
FIG. 1A illustrates a system according to an embodiment of the present technology.

FIG. 1A illustrates a system 100 according to an embodiment of the present technology. The system 100 is shown as including two leadless pacemakers (LPs) 102a and 102b located in or on different chambers of the heart, and a body worn device 122 shown as being a wrist worn device that is worn on a wrist. The LPs 102a and 102b can be referred to collectively as the LPs 102, or individually as an LP 102. The system 100 can include less than two LPs (e.g., just one LP), or more than two LPs. Further, the body worn device 122 can alternatively be designed to be worn on one or more other portions of a person's body besides a wrist, e.g., on an ankle or an upper arm, but is not limited thereto. Also shown in FIG. 1A is an external (i.e., non-implanted) programmer 109 that can communicate with the LPs 102. The one or more implanted LPs 102 can be referred to as an implanted or implantable subsystem. The implantable subsystem can include alternative and/or additional implantable devices, such as an ICD, as described below with reference to FIG. 1B. The body worn device 122 can also be referred to as a user-wearable device 122. In FIG. 1A, the user-wearable device 122 is also shown as be in communication with a base station 139, which can be a bedside monitor or personal advisory module (PAM), or can be a smartphone, a tablet computer, a personal data assistant (PDA), a laptop computer, a desktop computer, or some other computing device that is capable of performing wireless communication. The base station 139 can, e.g., include a health and fitness software application and/or other applications, which can be referred to as apps. The user-wearable device 122 can upload data obtained by the device 122 to the base station 139, so that such data can be used by a software application executed by the base station 139. The body worn device 122, the programmer 109, and/or the base station 139 can be referred to as a non-implanted or a non-implantable subsystem. The system 100 thus includes both an implantable subsystem and a non-implantable subsystem.

Figure 1B:
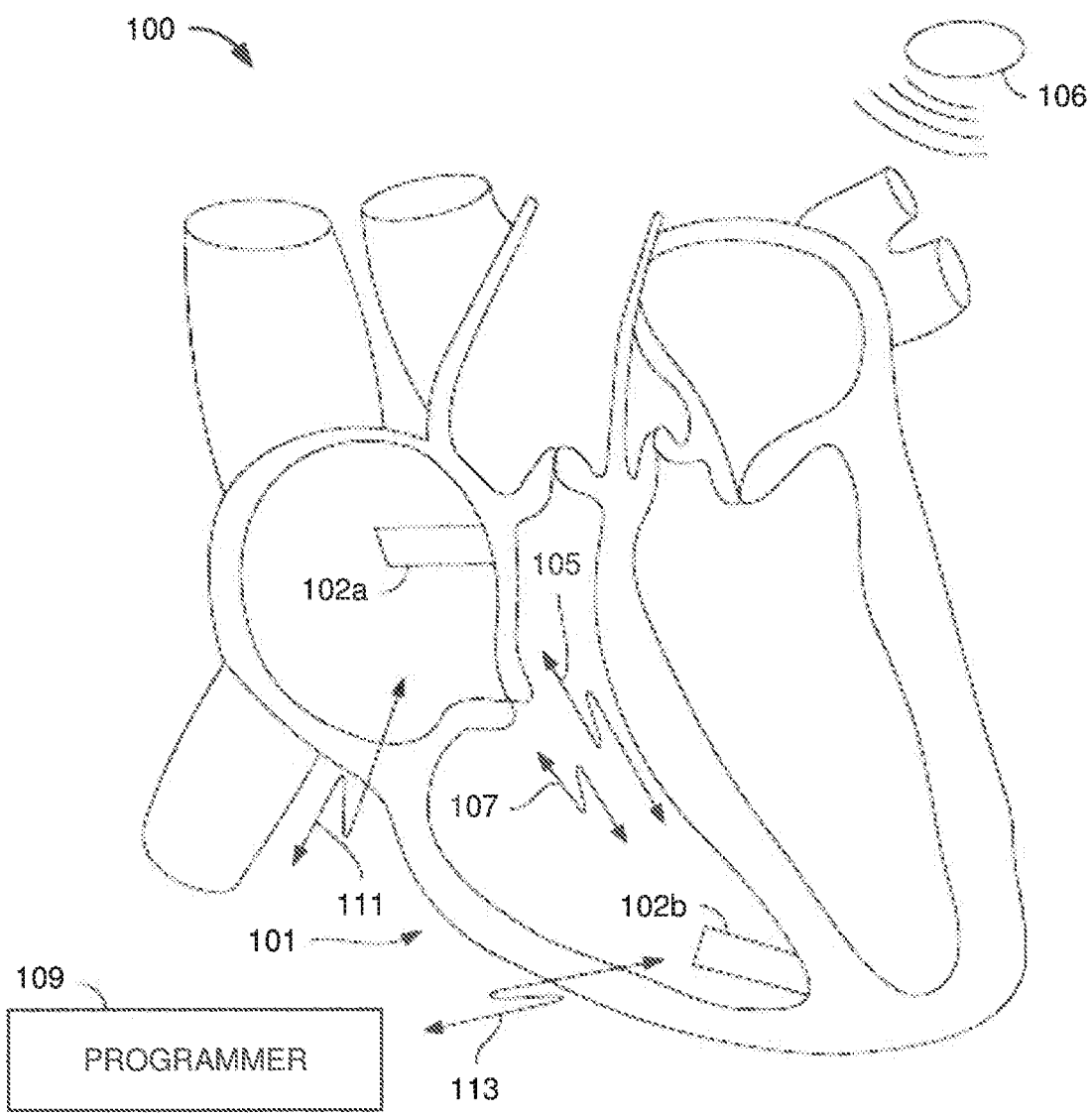
FIG. 1B illustrates exemplary locations at which leadless pacemakers (LPs) introduced in FIG. 1A can be implanted within the heart.

FIG. 1B illustrates exemplary cardiac locations at which the LPs 102a and 102b, introduced in FIG. 1A, can be implanted within the heart. In FIG. 1B the LP 102a is located in a right atrium, while the LP 102b is located in a right ventricle. The LPs 102a and 102b can communicate with one another to inform one another of various local physiologic activities, such as local intrinsic events, local paced events and the like. The LPs 102a and 102b may be constructed in a similar manner, but operate differently based upon which chamber the LP 102a or 102b is located.

In some embodiments, one or more LPs 102a and 102b can be co-implanted with an implantable cardioverter-defibrillator (ICD) 106. Each LP 102a, 102b uses two or more electrodes located within, on, or within a few centimeters of the housing of the pacemaker, for pacing and sensing at the cardiac chamber, for bidirectional communication with one another, with the programmer 109, and/or the ICD 106.

In some embodiments, the LPs 102a and 102b communicate with one another, with the ICD 106, and with the programmer 109 by conductive communication through the same electrodes that are used for sensing and/or delivery of pacing therapy. When conductive communication is maintained through the same electrodes as used for pacing, the system 100 may omit an antenna or telemetry coil in one or more of the LPs 102a and 102b. In accordance with certain embodiments of the present technology, the LPs 102 utilize conductive communication to communicate with one another as well as with one or more non-implantable devices, such as the programmer 109 and the body worn device 122. In FIG. 1A, the external programmer 109 is physically in contact with the skin of the patient via two programmer skin electrodes 115a and 115b (also referred to as surface electrodes), which can serve three functions. The programmer skin electrodes 115a and 115b can be referred to individually as a programmer skin electrode 115 (or a surface electrode 115), or collectively as programmer skin electrodes 115 (or surface electrodes 115). First, the electrodes 115 can be used transmit encoded information from the programmer 109 to the LPs or other IMD(s) using, e.g., a modulated signal at a medium frequency of 10 kHz to 100 kHz. Second, the programmer skin electrodes 115 can be used to receive information from individual LPs or other IMD(s) by detecting encoded information, which may or may not be included in the pacing pulses of the LP(s) or other type of pacemaker. Third, the programmer skin electrodes 115 can receive or sense a surface electrocardiogram for display and analysis by the programmer 109.

While the methods and systems described herein include examples primarily in the context of LPs, it is understood that certain methods and systems herein may be utilized with various other external and implanted devices. By way of example, the systems and methods of the present technology described herein may include and/or be used with other types of implantable medical devices (IMDs) implanted in a human, not just LPs. Examples of such other types of IMDs, with which embodiments of the present technology can be used, include a subcutaneous ICD (subQ ICD), as well as a more conventional type of pacemaker and/or ICD that includes a housing implanted in a pectoral region with leads having electrodes implanted within a patient's heart. Another type of IMD with which embodiments of the preset technology can be used include an implantable cardiac monitor (ICM) that does not provide any therapy. These are just a few examples which are not intended to be all encompassing. For much of the following discussion, the IMD will be assumed to be an LP. However, as just mentioned above, embodiments of the present technology can be used with alternative types of IMDs that are configured to perform conductive communication with one or more non-implanted device(s), such as the programmer 109 and/or the user-wearable device 122.

Exemplary Leadless Pacemaker

Figure 2:
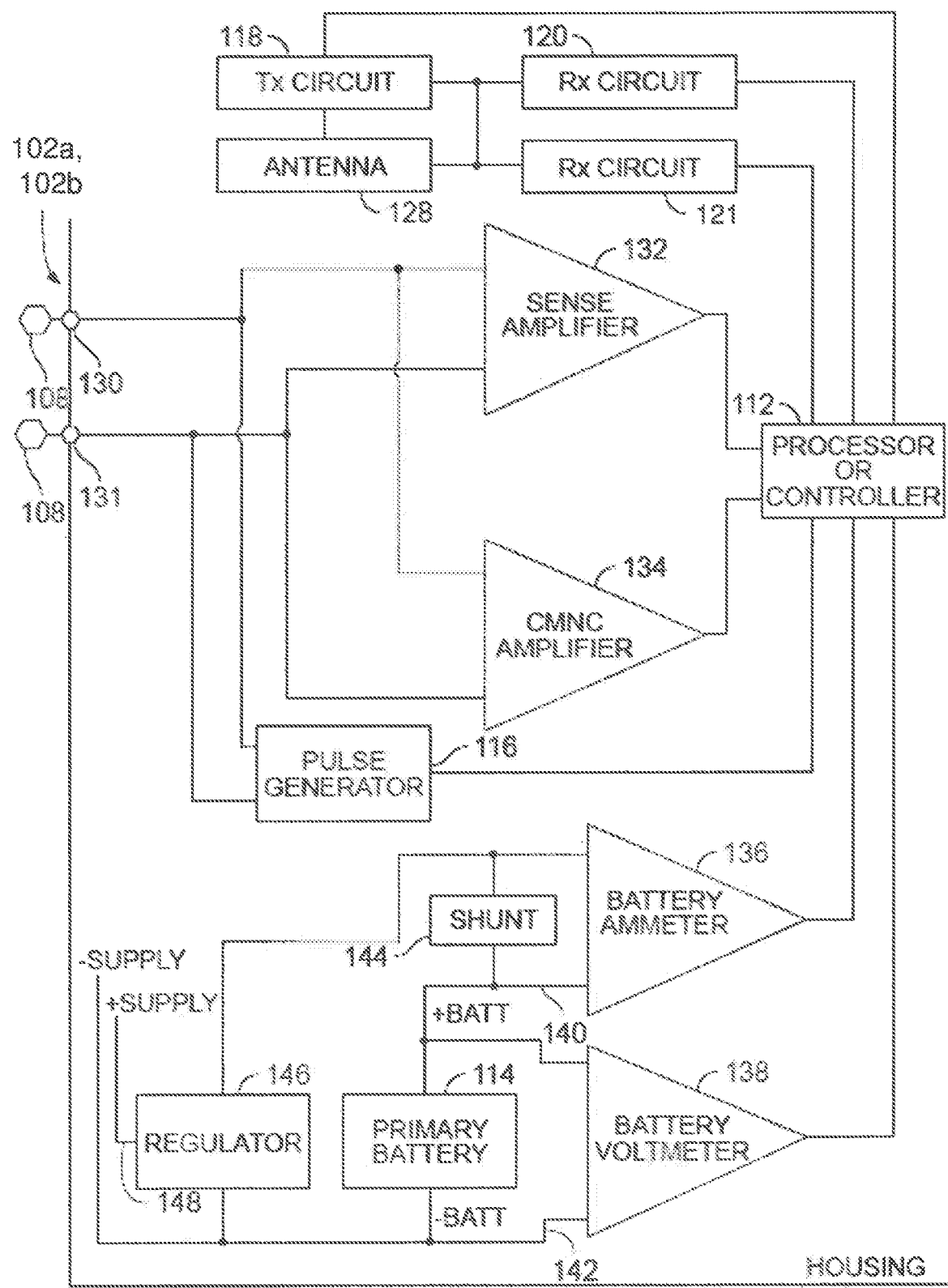
FIG. 2 is a block diagram of a single LP in accordance with certain embodiments herein.

Referring to FIG. 2, a pictorial diagram shows an embodiment for portions of the electronics within an LP 102 configured to provide conducted communication through the sensing/pacing electrodes. The LP 102 comprise at least two leadless electrodes 108 configured for delivering cardiac pacing pulses, sensing evoked and/or natural cardiac electrical signals, and perform uni-directional or bi-directional conductive communication. As noted above, an LP, such as the LP 102, is an example of an IMD that can perform conductive communications, and more specifically, can transmit and receive conductive communication signals.

In certain embodiments, the LPs 102a and 102b each includes a transmitter 118 and first and second receivers 120 and 121 that collectively define separate first and second communication channels 105 and 107 (FIG. 1), (among other things) between LPs 102a and 102b. Although first and second receivers 120 and 121 are depicted, in other embodiments, LP 102a, 102b may only include first receiver 120, or may include additional receivers other than first and second receivers 120 and 121. LP 102a, 102b may only also include one or more transmitters in addition to transmitter 118. In certain embodiments, LPs 102a and 102b may communicate over more than just first and second communication channels 105 and 107. In certain embodiments, LPs 102a and 102b may communicate over one common communication channel 105. In accordance with certain embodiments, the LPs 102a and 102b communicate conductively over a common physical channel via the same electrodes 108 that are also used to deliver pacing pulses. Usage of the electrodes 108 for conductive communication enables the LPs 102a and 102b to perform antenna-less and telemetry coil-less communication.

When LP 102a, 102b senses an intrinsic event or delivers a paced event, the corresponding LP 102a, 102b transmits an implant event message to the other LP 102a, 102b. For example, when an atrial LP 102a senses/paces an atrial event, the atrial LP 102a transmits an implant event message including an event marker indicative of a nature of the event (e.g., intrinsic/sensed atrial event, paced atrial event). When a ventricular LP 102b senses/paces a ventricular event, the ventricular LP 102b transmits an implant event message including an event marker indicative of a nature of the event (e.g., intrinsic/sensed ventricular event, paced ventricular event). In certain embodiments, LP 102a, 102b transmits an implant event message to the other LP 102a, 102b preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice or wakeup pulse) followed by an event marker. The notice trigger pulse is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any implant to implant (i2i) communication from another LP (or other IMD) or from an external device may transmit a receive acknowledgement indicating that the receiving LP/IMD received the i2i communication, etc. Where an i2i communication is performed using conductive communication, the i2i communication can be referred to more specifically as i2i conductive communication, or more generally as conductive communication.

The event messages enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments described herein provide efficient and reliable processes to maintain synchronization between LPs 102a and 102b without maintaining continuous communication between LPs 102a and 102b. In accordance with certain embodiments herein, the transmitter(s) 118 and receiver(s) 120, 122 utilize low power event messages/signaling between multiple LPs 102a and 102b. The low power event messages/signaling may be maintained between LPs 102a and 102b synchronously or asynchronously.

In certain embodiments, when LP transmitter 118 transmits event signals over a conductive communication channel that has an electrode load of 500 ohm using a 1 ms pulse width at 2.5V at a rate of 60 bpm, LP transmitter 118 will draw 4.4 µA for transmit current. When LP transmitter 118 transmits event signals at 2.5V using a 2 µs pulse width, transmitter 118 only draws 10 nA to transmit event messages at a rate of 60 bpm. In order to sense an event message (transmitted with the foregoing parameters), receivers 120 and 121 may utilize 50 µA. In accordance with certain embodiments herein, the pulse widths and other transmit/receive parameters may be adjusted to achieve a desired total (summed) current demand from both transmitter 118 and receivers 120 and 121. The transmitter current decreases nearly linearly with narrowing bandwidth (pulse width), while a relation between receiver current and bandwidth is non-linear.

In accordance with certain embodiments herein, LPs 102a and 102b may utilize multi-stage receivers that implement a staged receiver wakeup scheme in order to improve reliability yet remain power efficient. Each of LPs 102a and 102b may include first and second receivers 120 and 121 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/less than 10 µs per pulse) assigned to the second receive channel. First receiver 120 may maintain the first channel active (awake) for at least a portion of a time when the second channel is inactive (asleep) to listen for event messages from a remote LP. The controller or processor determines whether the incoming signal received over the first channel corresponds to an LP wakeup notice. The second receiver 121 may be assigned a second activation protocol that is a triggered protocol, in which the second receiver 121 becomes active (awake) in response to detection of trigger events over the first receive channel (e.g., when the incoming signal corresponds to the LP wakeup notice, activating the second channel at the local LP).

The marker message may represent a signature indicative of an event qualification to qualify a valid event marker pulse. The event qualification messages distinguish a message from spurious noise and avoid mistaking other signals as event messages having implant markers. The event message may be repeated to allow the LP receiver 120 multiple chances to "catch" the event qualification. Additionally or alternatively, the Tx and Rx LP 102a, 102b may implement a handshaking protocol in which the Tx and Rx LP 102a, 102b exchange additional information, such as to allow a response to follow the marker. The exchange of additional information may be limited or avoided in certain instances as the exchange draws additional power when sending and receiving the information. Optionally, the event message may be configured with additional content to provide a more robust event marker.

Transmitter 118 may be configured to transmit the event messages in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, programmer 109 may communicate over a programmer-to-LP channel, with LP 102a, 102b utilizing the same communication scheme. The external programmer may listen to the event message transmitted between LP 102a, 102b and synchronize programmer to implant communication such that programmer 109 does not transmit communication signals 113 until after an implant to implant messaging sequence is completed.

In accordance with certain embodiments, LP 102a, 102b may combine transmit operations with therapy. The transmit event marker may be configured to have similar characteristics in amplitude and pulse width to a pacing pulse and LP 102a, 102b may use the energy in the event messages to help capture the heart. For example, a pacing pulse may normally be delivered with pacing parameters of 2.5V amplitude, 500 ohm impedance, 60 bpm pacing rate, 0.4 ms pulse width. The foregoing pacing parameters correspond to a current draw of about 1.9 µA. The same LP 102a, 102b may implement an event message utilizing event signaling parameters for amplitude, pulse width, pulse rate, etc. that correspond to a current draw of approximately 0.5 µA for transmit.

LP 102a, 102b may combine the event message transmissions with pacing pulses. For example, LP 102a, 102b may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102a, 102b senses an intrinsic event, the transmitter sends a qualitatively similar event pulse sequence (but indicative of a sensed event) without adding the pace pulse remainder. As LP 102a, 102b longevity calculations are designed based on the assumption that LP 102a, 102b will deliver pacing therapy 100% of the time, transmitting an intrinsic event marker to another LP 102a, 102b will not impact the nominal calculated LP longevity.

In some embodiments, LP 102a, 102b may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102a, 102b increases an extent to which LP 102a, 102b uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102a, 102b may use larger pulse widths.

By combining event messages and low power pacing, LP 102a, 102b may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

In an embodiment, a communication capacitor is provided in LP 102a, 102b. The communication capacitor may be used to transmit event signals having higher voltage for the event message pulses to improve communication, such as when the LPs 102a and 102b experience difficulty sensing event messages. The high voltage event signaling may be used for implants with high signal attenuation or in the case of a retry for an ARQ (automatic repeat request) handshaking scheme.

When an LP 102a, 102b does not receive an event message within a select time out interval, LP 102a, 102b may resend an event message at a higher amplitude. As another example, LP 102a, 102b may perform an event signaling auto-level search wherein the LPs send event messages at progressively higher amplitude until receiving confirmation that an event message was received (or receiving a subsequent event message from another LP). For example, in DDD mode when the atrial or ventricular LP 102a, 102b does not see an event signal from LP 102a, 102b in the other chamber before its timeout interval it could automatically raise the amplitude of the event message, until the LPs 102a and 102b become and remain in sync. Optionally, LP 102a, 102b may implement a search hysteresis algorithm similar to those used for rate and amplitude capture to allow the lowest safe detectible amplitude to be determined.

The LPs 102a and 102b may be programmable such as to afford flexibility in adjusting the event marker pulse width. In some embodiments, different receiver circuits may be provided and selected for certain pulse widths, where multiple receivers may be provided on a common ASIC, thereby allowing the user to vary the parameters in an LP after implant.

In some embodiments, the individual LP 102a can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102a and shows the LP's functional elements substantially enclosed in a hermetic housing 110. The LP 102a has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more leadless cardiac pacemakers 102a and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102a, 102b can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1A, 1B, and 2, the system 100 may comprise an implantable cardioverter-defibrillator (ICD) 106 in addition to leadless cardiac pacemaker 102a, 102b configured for implantation in electrical contact with a cardiac chamber and for performing cardiac rhythm management functions in combination with the implantable ICD 106. The implantable ICD 106 and the one or more leadless cardiac pacemakers 102a, 102b configured for leadless intercommunication by information conduction through body tissue and/or wireless transmission between transmitters and receivers in accordance with the discussed herein.

In a further embodiment, a cardiac pacing system 100 comprises at least one LP 102 configured for implantation in electrical contact with a cardiac chamber and configured to perform cardiac pacing functions in combination with the co-implanted implantable cardioverter-defibrillator (ICD)

106. Each LP 102 comprise at least two leadless electrodes 108 configured for delivering cardiac pacing pulses, sensing evoked and/or natural cardiac electrical signals, and transmitting information to the co-implanted ICD 106. The electrodes 108 can also be used to perform conductive communication with an external device, such as the programmer 109 and/or the user-wearable device 122.

LP 102a, 102b can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102a, 102b receiving the communication decode the information and respond depending on location of the receiving pacemaker and predetermined system functionality.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102a. The shunt 144 enables the battery current monitor 136 to provide the processor 112 with an indication of battery current drain and indirectly of device health. The illustrative power supply can be a primary battery 114.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in an LP 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds. The controller 112 can also control conductive communication with an external device.

Figure 3:
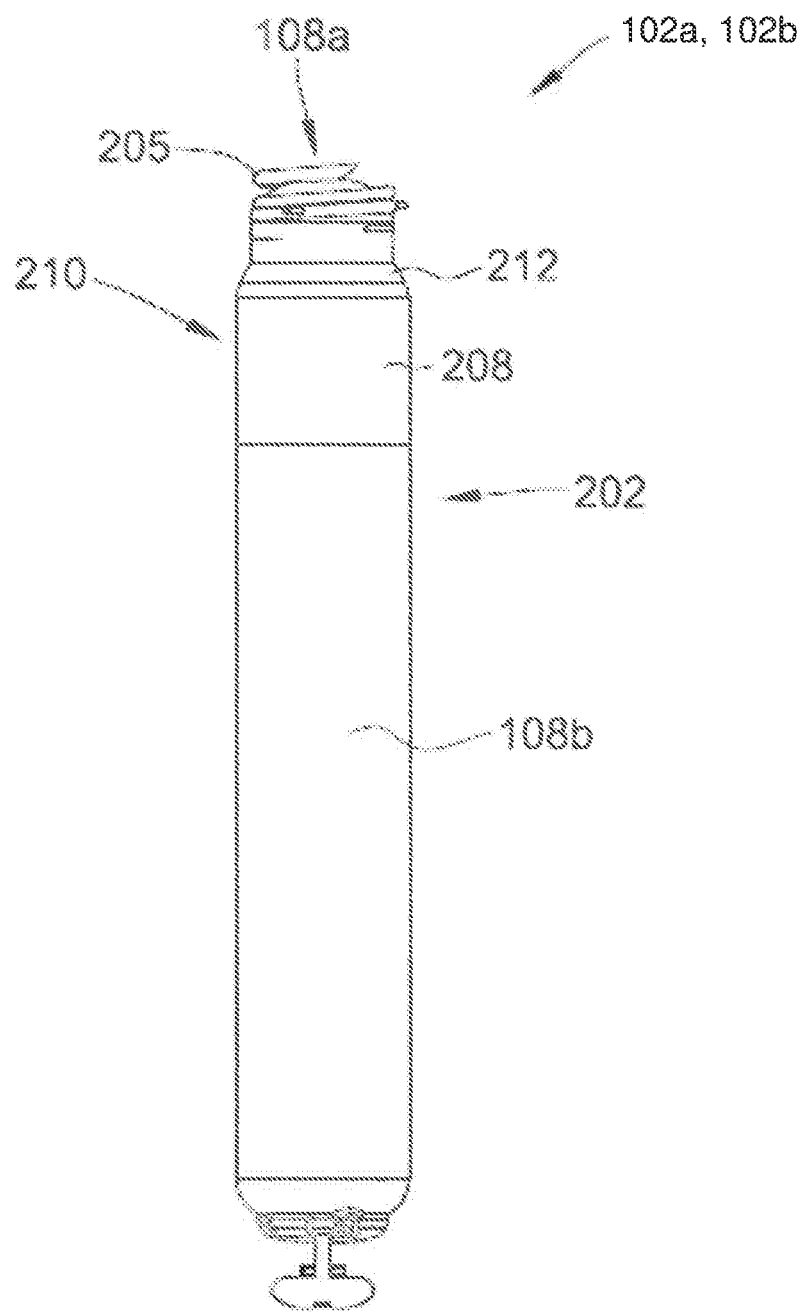
FIG. 3 illustrates an LP in accordance with certain embodiments herein.

FIG. 3 shows an LP 102a, 102b. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Exemplary Communication Pathway Between IMD and External Device

The LPs 102, or more generally one or more IMDs, can communicate with at least one external device (ED) via conductive communication. Conductive communication, which is sometimes also known as Intra-Body Communication (IBC) or Body Channel Communication (BCC), is a non-RF wireless data communication technique that uses the human body itself as the communication channel or transmission medium. Such communication may take place via communication pathways comprising a receiving pathway that decodes information encoded on pulses generated by one or more of the IMDs (e.g., LPs 102) and conducted through body tissue to the user-wearable device 122 and/or the programmer 109. According to the illustrative arrangement, the communication pathways can be configured for communication with multiple LPs 102 via two or more electrodes 108a and 108b and conduction through body tissue.

As will be described in additional detail with reference to FIGS. 6A and 6B, the user-wearable device 122, or more generally external device (ED), includes at least two electrodes that are in contact with the skin of the person wearing the device 122, e.g., on their wrist. In accordance with certain embodiments, the user-wearable device 122 is connected by a communication transmission channel and has receiving functional elements for receiving encoded information from one or more IMDs, such as one or more LPs 102. The communication channel includes two or more skin electrodes which can be in contact with the surface of the skin. From the point of the skin, the communication transmission channel is wireless, includes the ion medium of the intra- and extra-cellular body liquids, and enables electrolytic-galvanic coupling between the skin electrodes, which can also be referred to as surface electrodes, and the LPs, or more generally, IMDs.

In accordance with certain embodiments, information transmitted between an IMD and an ED can be conveyed by modulated signals at the approximate range of 10 kHz to 100 kHz which is a medium-high frequency, or at higher frequencies. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes.

In some embodiments, the one or more IMDs can comprise one or more LPs that generate cardiac pacing pulses and encode information onto the generated cardiac pacing pulses by selective alteration of pacing pulse morphology that is benign to therapeutic effect and energy cost of the pacing pulse. The cardiac pacing pulses conduct into body tissue via the electrodes for antenna-less and telemetry coil-less communication. For information transmitted from the LP(s) 102 to the user-wearable device 122, a communication scheme can be used in which the information is encoded on one or more pacing pulses. The pulse morphology is altered to contain the encoded information without altering the therapeutic benefits of the pacing pulse. The energy delivered by the pacing pulse remains essentially the same after the information is encoded. The user-wearable device 122 receives the pacing pulses through the associated surface electrodes. Encoded information is drawn from one or more pacing pulses and can contain various types of information, including an indication of when a ventricular depolarization occurred.

The LPs 102 can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. Communication bandwidth is low with only a small number of bits encoded on each pulse.

In some embodiments, information can be encoded using a technique of gating the pacing pulse for very short periods of time at specific points in the pacing pulse. During the gated sections of the pulse, no current flows through the electrodes of an LP. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the LP. A gated segment is set sufficiently long in duration to enable accurate detection by the programmer 109, limiting the amount of information that can be transmitted during a single pacing pulse. Accordingly, a technique for communication can comprise generating stimulation pulses on stimulating electrodes of an IMD and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted biostimulator and encoding information onto generated stimulation pulses comprising selectively varying timing between consecutive stimulation pulses.

Alternatively or in addition to encoding information in gated sections and/or pulse interval, overall pacing pulse width can be used to encode information. Non-pacing pulses can additionally or alternatively be used to transmit conductive communication signals.

The exemplary described methods of encoding information on pacing pulses can use the external programmer 109 to distinguish pacing pulses from the patient's normal electrocardiogram, for example by recognition of the specific morphology of the pacing pulse compared to the R-wave generated during the cardiac cycle. For example, the external programmer 109 can be adapted to distinguish a generated cardiac pacing pulse from a natural cardiac depolarization in an electrocardiogram by performing comparative pattern recognition of a pacing pulse and an R-wave produced during a cardiac cycle.

The illustrative external programmer 109 and associated operating methods or techniques enable presentation to a user of information gathered from the LPs 102 and/or 104 and or other IMD(s) using conductive communication. Some of the information to be presented may include battery voltage, lead impedance, electrocardiogram amplitude, or current drain of the device. The information can be presented in addition to other information such as parameters to be set and programmed into the LP. The information can be presented to a user on a display screen. Some embodiments or configurations of an external programmer 109 can include a secondary link, for example either wireless or through a cable, to another display device, such as a handheld computer or terminal. The secondary link can also include communication over a local area network or the internet for display at a remote terminal.

Event Messaging

LPs 102a and 102b can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102a and LP 102b operate as two independent leadless pacers maintaining beat-to-beat dual-chamber functionality via a "Master/Slave" operational configuration. For descriptive purposes, the ventricular LP 102b shall be referred to as "vLP" and the atrial LP 102a shall be referred to as "aLP". LP 102a, 102b that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes). Such i2i communications can be performing using conductive communications.

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
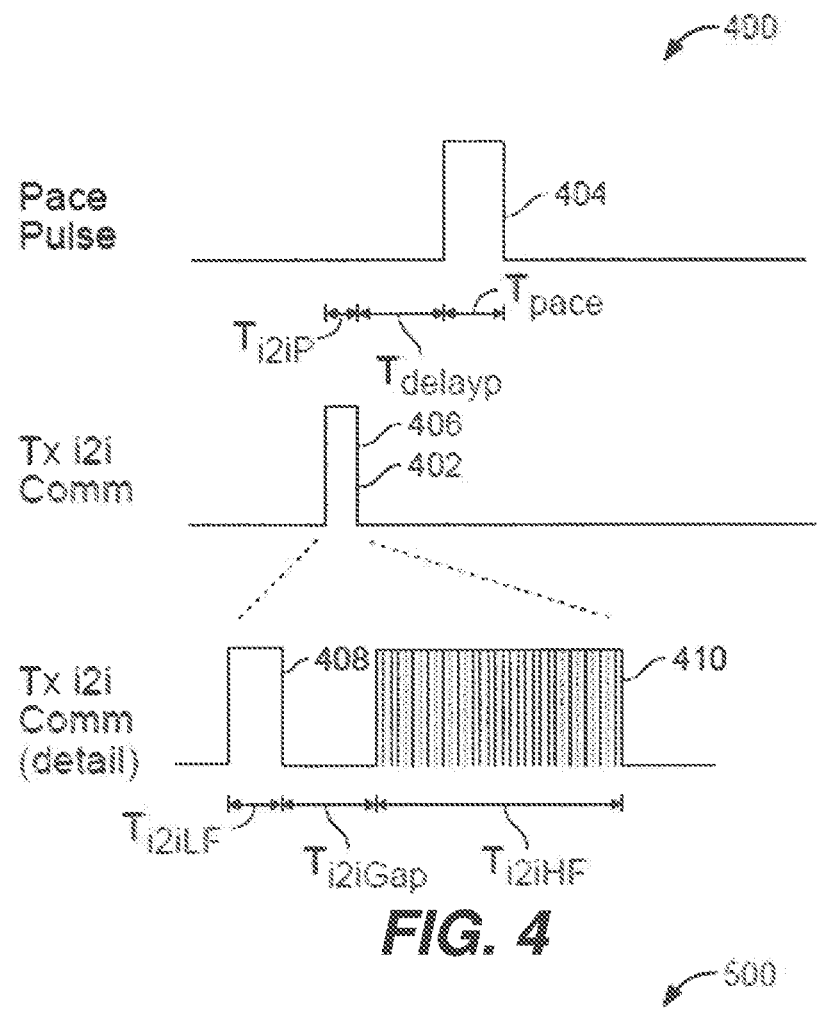
FIG. 4 is a timing diagram demonstrating one embodiment of implant to implant (i2i) communication for a paced event, and more generally, is a timing diagram for an exemplary conductive communication signal.

FIG. 4 is a timing diagram demonstrating one embodiment of implant to implant (i2i) communication for a paced event, and more generally, is a timing diagram for an exemplary conductive communication signal. The i2i communication may be transmitted, for example, from LP 102a to LP 102b. As shown in FIG. 4, in this embodiment, an i2i transmission 400 is sent prior to delivery of a pace pulse 404 by the transmitting LP (e.g., LP 102a). This enables the receiving LP (e.g., LP 102b) to prepare for the remote delivery of the pace pulse. The i2i transmission 400 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$. The transmission 400 is an example of a conductive communication signal. Such a conductive communication signal can alternative or additionally be received by an external device, such as the body worn device 122.

As shown in FIG. 4, the i2i transmission 400 lasts for a period Ti2iP, and pace pulse 404 lasts for a period Tpace. The end of i2i transmission 400 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 5:
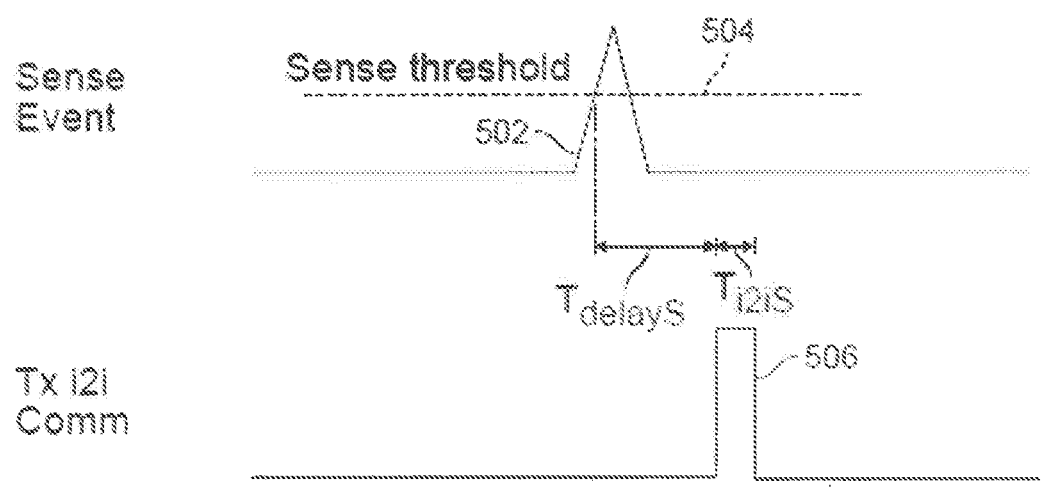
FIG. 5 is a timing diagram demonstrating one embodiment of i2i communication for a sensed event, and more generally, is a timing diagram for another exemplary conductive communication signal.

FIG. 5 is a timing diagram demonstrating one embodiment of i2i communication for a sensed event, and more generally, is a timing diagram for another exemplary conductive communication signal. The i2i communication may be transmitted, for example, from LP 102a to LP 102b. A same or similar type of communication can be used by an LP (or other IMD) to inform an external device, such as a body worn device discussed below, of a sensed event (e.g., a sensed intrinsic ventricular depolarization). As shown in FIG. 5, in this embodiment, the transmitting LP (e.g., LP 102a) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 400, i2i transmission 506 may include an envelope that may include one or more individual pulses. For example, similar to envelope 406, the envelope of i2i transmission 506 may include a low frequency pulse followed by a high frequency pulse train. The transmission 500 is another example of a conductive communication signal that can be detected by an external device, such as the body worn device 122.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay. An external device, such as the body worn device 122, can be configured to recognize the aforementioned markers to thereby know what type of conductive communication signal it receives.

User-Wearable Device

Figures 6A, 6B:
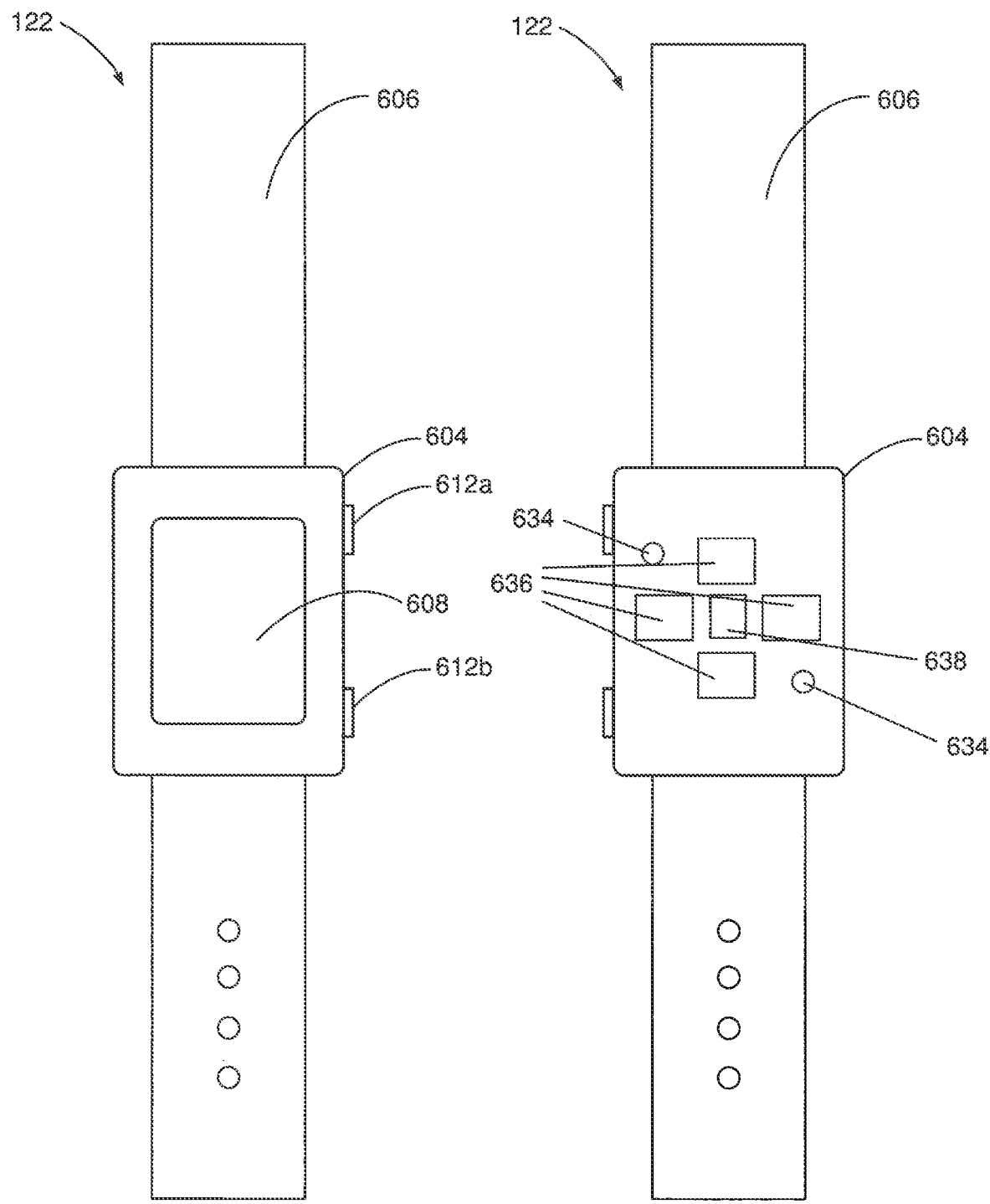
FIG. 6A depicts a front view of a user-wearable device, according to an embodiment.
FIG. 6B depicts a rear view of the user-wearable device of FIG. 6A, according to an embodiment.

FIGS. 6A and 6B depict, respectively, front and rear views of the user-wearable device 122, according to an embodiment. As noted above, the user-wearable device 122 can also be referred to as a body worn device, and can be referred to more generally as a non-implanted or non-implantable subsystem, or as an external device (ED).

The user-wearable device 622 can gather and processes data and displays results to a user. In accordance with certain embodiments, the user-wearable device 622 can receive conductive communication signals that are transmitted by in implanted device, such as an LP 102 or other type of IMD, and can use the conductive communication signals to monitor the blood pressure of the person wearing the device 622, as will be described in additional detail below. In certain embodiments, the user-wearable device 622 can wirelessly communicate with a base station (e.g., 139 in FIG. 1A), which can be a mobile phone, a tablet computer, a personal data assistant (PDA), a laptop computer, a desktop computer, or some other computing device that is capable of performing wireless communication. The base station can, e.g., include a health and fitness software application and/or other applications, which can be referred to as apps. The user-wearable device 122 can upload data obtained by the device 122 to the base station, so that such data can be used by a health and fitness software application and/or other apps stored on and executed by the base station.

The user-wearable device 622 is shown as including a housing 604, which can also be referred to as a case 604. A band 606 is shown as being attached to the housing 604, wherein the band 606 can be used to strap the housing 604 to a user's wrist, arm, or ankle, but not limited thereto. Where the user-wearable device 622 includes the wrist type band 606, the device 602 can also be referred to as a wrist-wearable or wrist-worn device. A front side of the housing 604 is shown as including a digital display 608, which can also be referred to simply as a display. The digital display 608 can be used to show the time, date, day of the week and/or the like. The digital display 608 can also be used to display physiological metrics, such as, but not limited to, heart rate (HR) and blood pressure (BP), as well as provide alerts and/or instructions. For example, in accordance with certain embodiments of the present technology, the digital display 608 may inform a user when their blood pressure is outside of an acceptable range. These are just a few examples of the types of information that may be displayed on the digital display 608, which are not intended to be all encompassing. As the terms are used herein, the terms user, wearer, person and patient are typically used interchangeably.

The housing 604 is further shown as including buttons 612a, 612b, which can individually be referred to as a button 612, and can collectively be referred to as the buttons 612. One of the buttons 612 can be a mode select button, while another one of the buttons 612 can be used to start and stop certain features. While the user-wearable device 622 is shown as including two buttons 612, more or less than two buttons can be included. The buttons 612 can additionally or alternatively be used for other functions. While the shapes of the housing 604 and the digital display 608 are shown as generally being rectangular, they can alternatively have other shapes, such as, but not limited to, circular or oval shapes.

In certain embodiments, the user-wearable device 622 can receive alerts from a base station (e.g., 139 in FIG. 1A), or can generate its own alerts. For example, where the base station 139 is a smartphone, the user-wearable device 622 can receive alerts from the base station, which can be displayed to the user on the display 608. For a more specific example, if a smartphone type of base station 139 is receiving an incoming phone call, then an incoming phone call alert can be displayed on the digital display 608, which alert may or may not include the phone number and/or identity of the caller. Other types of alerts include, e.g., blood pressure alerts, text message alerts, social media alerts, calendar alerts, medication reminders and exercise reminders, but are not limited thereto. Such alerts can be generated solely by the user-wearable device 622, or with the assistance of a base station (e.g., 139) or implanted device (e.g., 102) with which the user-wearable device 122 wirelessly communicates. The user-wearable device 622 can inform the user of a new alert by vibrating and/or emitting an audible sound.

FIG. 6B illustrates an exemplary rear-view of the housing or case 604 of the user-wearable device 622. Referring to FIG. 6B, the backside of the housing 604, which can also be referred to as a caseback, is schematically shown as including two electrodes 634 (also referred to as electrode contacts 634) that are spaced apart from one another, four light emitting elements 636, and a light detecting element 638. The user-wearable device 622 can include as few as one light emitting element 636 and/or more than one light detecting element 638. The one or more light emitting element 636 and the one or more light detecting element 638 collectively provide an optical sensor. Such an optical sensor can be used to obtain a photoplethysmography (PPG) signal, as will be discuss in further detail below. Where the optical sensor is used to obtain a PPG signal, the optical sensor can also be referred to as a PPG sensor. Accordingly, the light emitting element(s) 636 and the light detecting element(s) 638 can collectively provide a PPG sensor. The light emitting element(s) 636 can include one or more light emitting diode (LED), incandescent lamp or laser diode, but is not limited thereto. While infrared (IR) light sources are often employed in optical sensors, because the human eye cannot detect IR light, the light source can alternatively produce light of other wavelengths. The light detecting element(s) 638 can include one or more one or more photoresistor, photodiode, phototransistor, photodarlington or avalanche photodiode, but is not limited thereto.

As noted above, the light emitting elements 636 and the light detecting element 638 are components of an optical sensor, which can be a PPG sensor. The optical sensor can alternatively include as few as one light emitting element, two or three light emitting elements, or more than four light emitting element. The light emitting elements may all be of the same color, or multiple colors, depending on the one or more physiological parameter(s) being monitored, e.g., blood volume, oxygenation level, and/or other parameters. It is also possible that the optical sensor includes multiple light detecting elements 638. The light emitting element(s) and light detecting element(s) of the optical sensor are likely covered by light transmissive windows that protect the light emitting element(s) and light detecting element(s).

As noted above, the backside of the housing 604 of the user-wearable device 122 is shows as including two electrodes 634. Such electrodes 634 can be used to obtain an impedance plethysmography signal (IPG). Where such electrodes 634 are used to obtain an IPG signal, the electrodes 634 can be considered part of an IPG sensor.

In FIGS. 6A and 6B the housing 604 of the user-wearable device 122 was described as being attachable to a patient using a strap 606. In alternative embodiments, the user-wearable device 122 can be a patch that is attachable to a patient's body via an adhesive or the like. Other form factors of the user-wearable device 122 are also possible.

Figure 7:
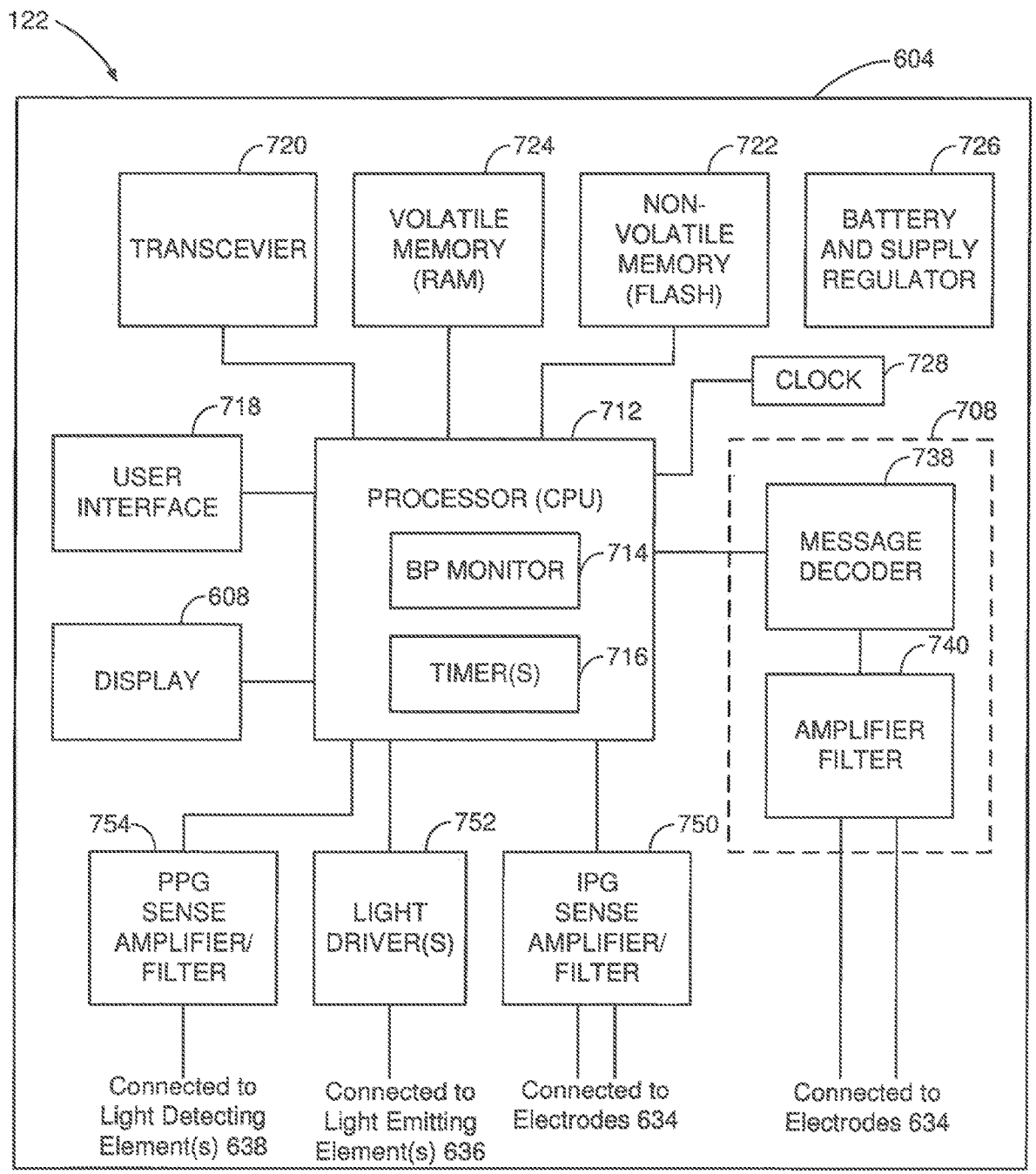
FIG. 7 illustrates a block diagram of the user-wearable device, introduced in FIGS. 6A and 6B, according to an embodiment of the present technology.

FIG. 7 illustrates a schematic block diagram of the user-wearable device 122, introduced in FIGS. 6A and 6B, according to an embodiment of the present technology. The user-wearable device 122 is an example of an external device (ED), and thus, can also be referred to as an external device (ED), or more succinctly, a device 122. The device 122 is shown as including one or more processors 712, a user interface 718, a transceiver 720, volatile memory 724, non-volatile memory 722, a battery and supply regulator 726, a conductive communication receiver 708. The conductive communication receiver 708 is shown as including amplifier and filter circuitry 740 and a message decoder 738. The amplifier and filter circuitry 740 which is coupled to at least two electrodes 634 that are configured to be on contact with the skin of a person wearing the device 122. As mentioned with reference to FIG. 6A, the device 122 also includes a display 608. The display 608 can be used to show the time, date, day of the week and/or the like. The display 608 can also be used to display physiological metrics, such as, but not limited to, heart rate (HR) and blood pressure (BP), as well as provide alerts and/or instructions. The user interface 718 can enable a user to select among the various functions of and information that may be displayed by the device 122. The user interface 718 can be a touch screen, and thus, be part of the display 608. Alternatively, or additionally, the user interface 718 can include one or more buttons, and/or the like.

The device 122 is also shown as including IPG sense amplifier and filter circuitry 750 which is coupled to at least two electrodes 634 and is configured to sense an IPG signal. The IPG sense amplifier and filter circuitry 750 can provide an IPG sensor that is used to sense an IPG signal that is provided to the processor 712. The IPG sense amplifier and filter circuitry 750 can include an analog to digital converter that converts the IPG signal to a digital signal before it is provided to the processor 712.

The device 122 is further shown as including one or more light driver(s) 752 coupled to one or more light emitting element(s) 636 and PPG sense amplifier and filter circuitry 754 which is coupled to one or more light detecting element(s) 638. The light driver(s) 752, light emitting element(s) 636, light detecting element(s) 638, and PPG sense amplifier and filter circuitry 754 can make up a PPG sensor. The light driver(s) 752 drive the light emitting element(s) 636, under the control of the processor 712, to cause the emission of light. The light detecting element(s) 638 detect reflect/backscattered light. In this manner, changes in reflected light intensity are detected by the light detector, which outputs a PPG signal indicative of the changes in detected light, which are indicative of changes in blood volume. The PPG sense amplifier and filter circuitry 754 amplifies and filters signals produced by the light detecting element(s) 638, to thereby produce a filtered and amplified PPG signal that is provided to the processor 712. The PPG signal can additionally be converted from an analog signal to a digital signal, by an analog-to-digital converter, before being provided the processor 712. In other words, the PPG sense amplifier and filter circuitry 754 can also include an analog to digital converter that converts the PPG signal to a digital signal before it provided to the processor 712. In the above described embodiment, the light emitting element(s) and the light detecting element(s) are configeured in a reflection arrangement where the light emitting element(s) and the light detecting element(s) are mounted adjacent to one another on a surface of a body. In alternative embodiments, the light emitting element(s) and the light detecting element(s) can be configured in a transmission arrangement, where the light emitting element(s) and the light detecting element(s) face one another and a segment of the body (e.g., a wrist, finger or earlobe) is interposed between the light emitting element(s) and the light detecting element(s).

While the device 122 is described as including both a PPG sensor and an IPG sensor, it is possible that the device 122 includes only one of a PPG sensor and an IPG sensor. Each cardiac cycle in a plethysmography signal (which can be a PPG or IPG signal) generally appears as a peak, thereby enabling a plethysmography signal to be used to detect peak-to-peak intervals, which can be used to calculate heart rate (HR) and heart rate variability (HRV), if desired.

The amplifier and filter circuitry 740 amplify and filter conductive communication signals that are transmitted through patient tissue by an IMD that is implanted within the patient that is wearing the device 122, before such signals are provide to the message decoder 738. The message decoder 738 decodes conductive communication signals received by the device 122. The type of decoding performed by the message decoder 738 depends upon the type of encoding that was used by the IMD. Exemplary encoding techniques that may be used include, but are not limited to, on-off keying, frequency-shift keying, frequency modulation, and amplitude shift keying. The decoded messages are provided to the processor 712, which can use the decoded messages to monitor the patient's blood pressure and/or changes therein. The processor 712 can determine whether specific conductive communication signals indicate the occurrence of ventricular depolarization of the patient's heart, and if so, can used such an indication to monitor the patient's blood pressure, in manners described herein. More specifically, the processor 712 can include a BP monitor module 714 that can perform certain steps described below with reference to FIG. 9 to monitor the patient's blood pressure and/or changes therein. The BP monitor module can be implemented in software, firmware, hardware, or combinations thereof.

The processor 712 is coupled to a transceiver 720 which enables the device body worn device 122 to communicate wirelessly with a base station (e.g., 139 in FIG. 1), which can be a bedside monitor or personal advisory module (PAM), or can be a smartphone, a tablet computer, a personal data assistant (PDA), a laptop computer, a desktop computer, or some other computing device that is capable of performing wireless communication.

The processor 712 can execute operations based on firmware stored in non-volatile memory (Flash) 722. The non-volatile memory 722 can also be used to store parameters or values that are to be maintained when power is removed.

The processor 712 uses volatile memory or random access memory (RAM) 724 as general storage for information such as BP data, ECG data, status information, swap memory, and other data. A battery and supply regulator 726 give a constant voltage supply to the device 122 during normal operation. A clock module 728 generates a system clock signal used by the processor 712 and other blocks for timing.

Figure 8:
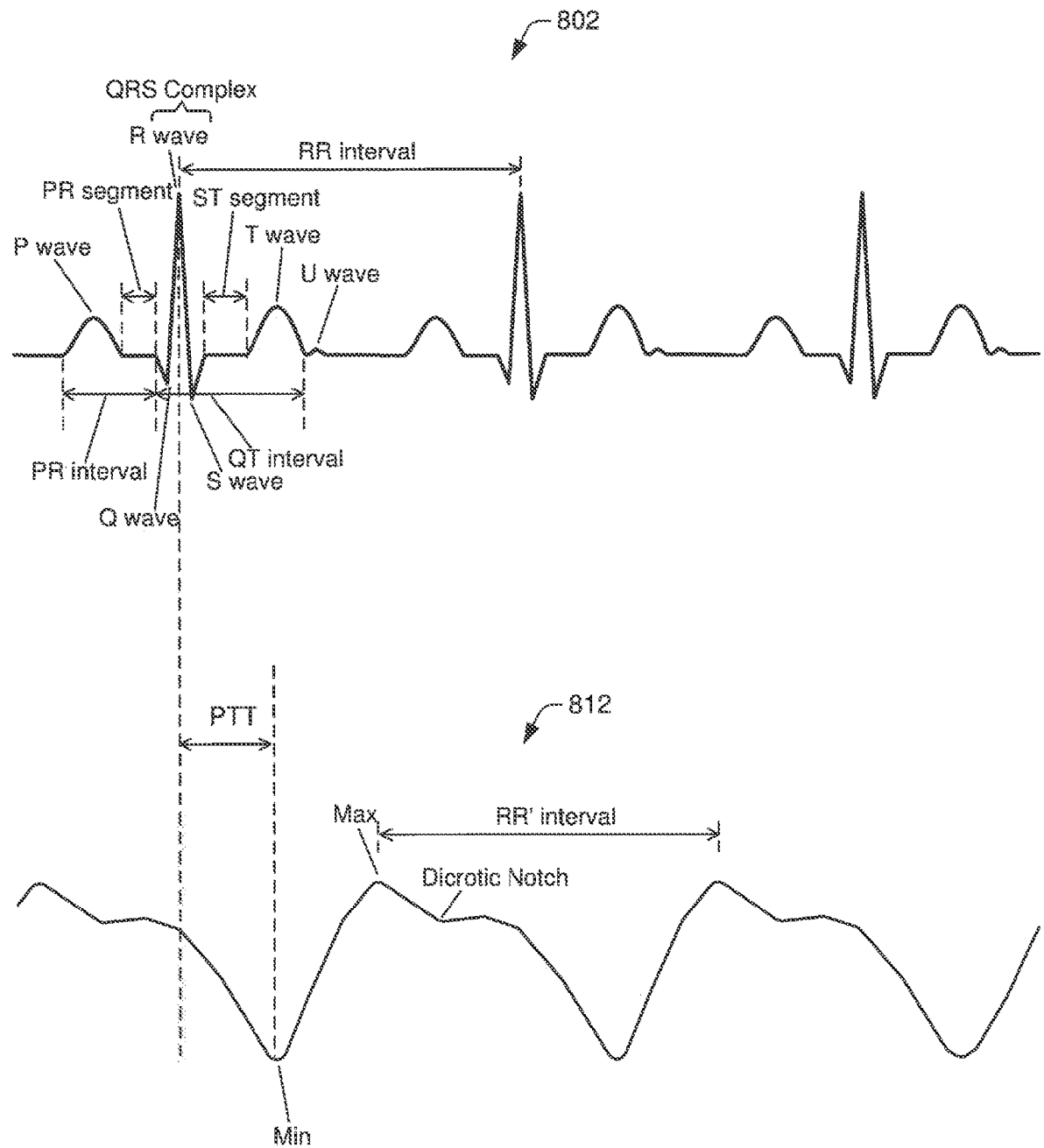
FIG. 8 illustrates idealized drawings of portions of an electrocardiogram (EGM) signal and a plethysmography signal, wherein the plethysmography signal can be a photoplethysmography (PPG) signal or an impedance plethysmography (IPG) signal.

FIG. 8 illustrates idealized drawings of portions of an electrogram (EGM) signal 802 and a plethysmography signal 812, wherein the plethysmography signal can be a photoplethysmography (PPG) signal or an impedance plethysmography (IPG) signal. The EGM signal 802 can also be referred to as an EGM waveform 802. The plethysmography signal 812 can also be referred to as a plethysmography waveform 812, and depending upon the specific implementation, as an PPG waveform or an IPG waveform, or more generally as a plethysmography (PG) signal.

The EGM signal 802 can be obtained using electrodes of an IMD, e.g., using the electrodes 108 of an LP 102, but not limited thereto. In other words, the EGM signal 802, which is indicative of cardiac electrical activity, can be sensed by an IMD. Where the plethysmography signal 812 is a PPG signal, the PPG signal can be sensed by an optical sensor (including one or more light emitting elements 636 and one or more light detecting elements 638) of the user wearable device 122. Where the plethysmography signal 812 is an IPG signal, the IPG signal can be sensed by an IPG sensor (including at least two electrodes 634) of the indicative of variations in blood volume in a region of the patient user wearable device 122. Either way, the plethysmography signal 812 is indicative of variations in blood volume in a region of the patient adjacent to the sensor that obtains the plethysmography signal 812.

Referring to the EGM signal 802 in FIG. 8, each cycle of the signal 802 is shown as including a P wave, a QRS complex (including Q, R and S waves), a T wave and a U wave. The P wave is caused by depolarization of the atria. This is followed by an atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. The Q, R, and S waves occur in rapid succession, and reflect a single event, and thus are usually considered together as the QRS complex. The Q wave is any downward deflection after the P wave. An R wave follows as an upward deflection, and the S wave is any downward deflection after the R wave. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole. Also shown in the exemplary EGM signal 802 is a U wave, which may not always be observed as a result of its small size, and which is thought to represent repolarization of the Purkinje fibers.

Also shown in FIG. 8 are various different intervals and segments that can be measured from an EGM signal, such as the EGM signal 802. These various intervals and segments are examples of features of an EGM signal. These include the PR interval, the QT interval, the RR interval, the PR segment, and the ST segment. The PR interval, which is sometimes referred to as the PQ interval, is the period that extends from the beginning of the P wave (the onset of atrial depolarization) until the beginning of the QRS complex (the onset of ventricular depolarization), and is normally between about 120 and 200 milliseconds (ms) in duration. The length and/or variability of the PR interval can be used to monitor for certain medical conditions, such as, but not limited to, heart block and pericarditis. The QT interval, which is the period that extends from the beginning of the Q wave until the end of the T wave, represents electrical depolarization and repolarization of the ventricles. A lengthened QT interval is a marker for the potential of ventricular tachyarrhythmias like torsades de pointes and a risk factor for sudden death. The RR interval is the period between R waves, or more generally, between QRS complexes, and is indicative of the heart rate (HR). For example, HR in beats per minute (bpm) can be determined by measuring a plurality of RR intervals, calculating an average RR interval, and dividing the number sixty (60) by the average RR interval. RR intervals can also be used to measure heart rate variability (HRV), which is the physiological phenomenon of variation in the time interval between heartbeats, which has been shown to be predictor of mortality after myocardial infarction. Additionally, a low HRV is believed to be an indicator of other conditions, such as congestive heart failure and diabetic neuropathy. The PR segment is the period that extends from the end of the P wave to the beginning of the QRS complex. PR segment abnormalities can be indicative of pericarditis or atrial ischemia. The ST segment is the period that extends from the end of the S wave (or the end of the QRS complex) to the beginning of the T wave, and is normally between about 80 and 120 ms in duration. A normal ST segment has a slight upward concavity. A flat, downsloping, or depressed ST segments, may indicate coronary ischemia. ST elevation may indicate transmural myocardial infarction. ST depression may be associated with subendocardial myocardial infarction, hypokalemia, or digitalis toxicity.

Referring to the plethysmography signal 812 in FIG. 8, each cycle of the plethysmography signal 812 is shown as including a minimum (min), a maximum (max), and a dicrotic notch that follows the max. However, it should be noted that the dicrotic notch may sometimes not be identifiable. The portion of the plethysmography waveform from a minimum to a following maximum shall also be referred to herein as the initial portion of the plethysmography waveform. The portion of the plethysmography waveform from a maximum to the following minimum shall be referred to as the terminal portion of the plethysmography waveform. The dicrotic notch, which is located in the terminal portion of the PPG waveform, is the first local minimum following a maximum in the plethysmography waveform.

Ventricular depolarization occurs at the beginning of systole, which substantially coincides with the end of diastole. The maximum peak amplitude of the plethysmography signal 812 occurs when a mechanical pulse resulting from the ventricular depolarization is detected by the plethysmography sensor, which is a distance from a location in the person's heart where the pulse originated. More specifically, the maximum (also referred to as peak) of the plethysmography signal 812 occurs at a time after the peak in the arterial blood pressure in the aorta at the level of the left ventricular outflow tract (note that this is representative of the time of peak pressure in the region illuminated by the plethysmography sensor). This is because the peak in the plethysmography signal 812 is indicative of the peak wave in arterial blood pressure generated by the person's heart, as detected by a plethysmography sensor located a distance from the person's heart. For example, if the plethysmography sensor is located adjacent to a person's wrist, it may take a pulse wave (as detected from EGM electrodes) on the order of about 200-250 ms to travel from the person's heart to the PPG sensor. Stated another way, a few hundreds of milliseconds after the QRS complex in an EGM signal, the plethysmography amplitude reaches a minimum and then starts to increase. This is due to the increasing blood volume in the arterioles as the systolic pulse reaches the periphery. The delay is influenced by the distance that the plethysmography sensor is placed from the heart. It requires approximately 100 ms for the amplitude of the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

As will be described in additional detail below, certain embodiments of the present technology can be used to monitor a patient's blood pressure, and/or changes therein, based on a time delay (TD) that is indicative of how long it takes a pulse wave to travel from a patient's heart to a peripheral region of the patient's body. Specific such embodiments are described below with reference to the flow diagram of FIG. 9.

Figure 9:
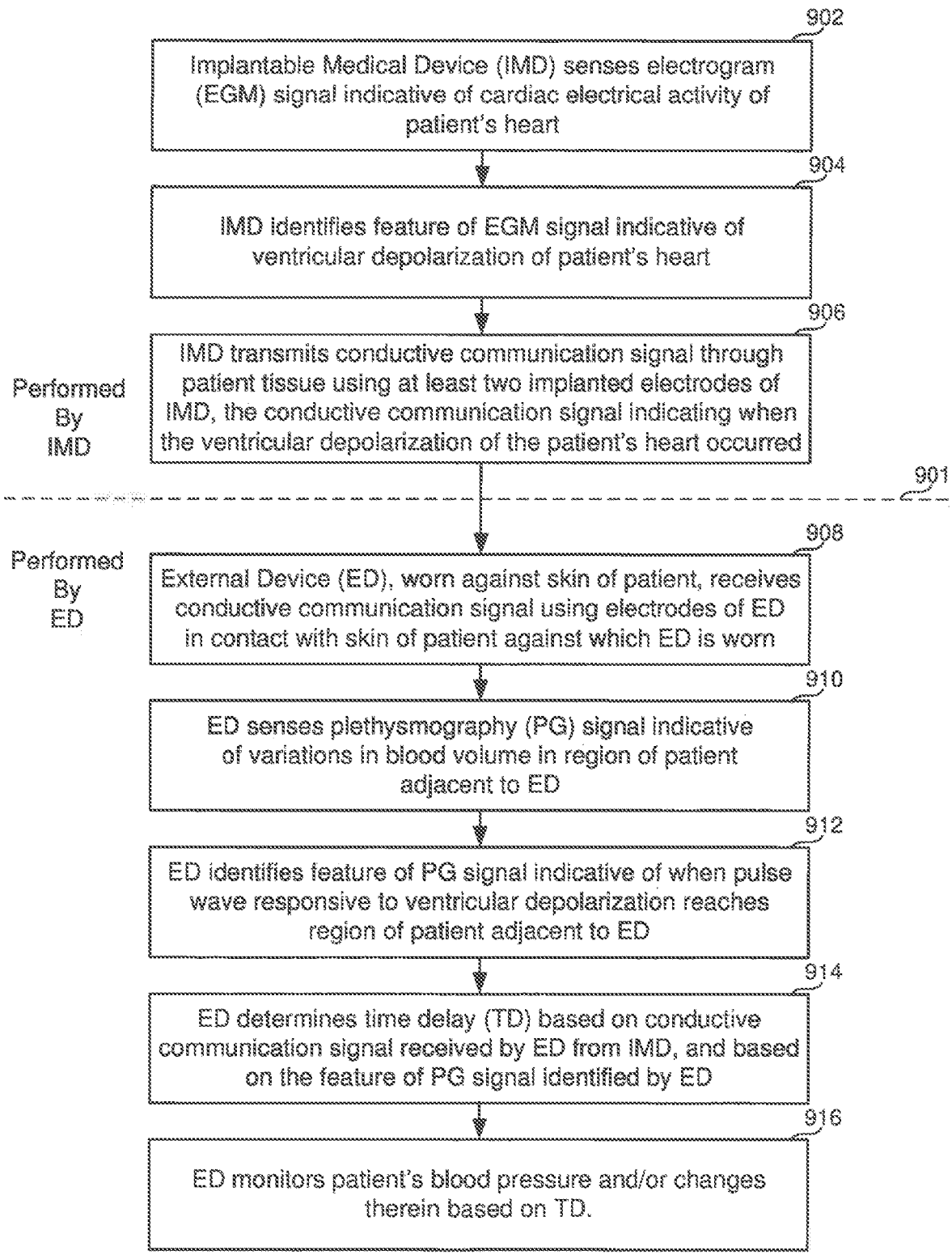
FIG. 9 is a flow diagram that is used to summarize methods according to certain embodiments of the present technology.

Referring to FIG. 9, the steps shown above the dashed line 901 are performed by an implantable medical device (IMD), and the steps shown below the dashed line 901 are performed by an external device (ED). The IMD can be a leadless pacemaker (LP) that is the same as or similar to an LP 102 described above with reference to FIGS. 1A, 1B, 2, and 3, but is not limited thereto. The IMD can alternatively be some other type of implantable medical device that includes at least two electrodes and is capable of transmitting conductive communication signals. For example, the IMD can alternatively be a more conventional type of pacemaker and/or ICD that includes one or more leads that extend from a housing located in a pectoral region into a patient's heart. The ED can be a body worn device that is the same as or similar to the body worn device 122 described above with reference to FIGS. 6A and 6B, but is not limited thereto. As can be appreciated from the below discussion, the steps that are described with reference to FIG. 9 relate to a method for use in monitoring a patient's blood pressure.

Referring to FIG. 9, step 902 involves an IMD sensing an electrogram (EGM) signal indicative of cardiac electrical activity of the patient's heart. Such an EGM signal can be sensed using two or more electrodes of the IMD. For example, referring back to FIGS. 2 and 3, the EGM signal can be sensed using electrodes 108 of an LP 102. Electrodes of a lead of a more conventional type of pacemaker can alternatively be used to sense an EGM signal, as could subQ electrodes of a subQ ICD. The portion of the EGM signal 802 shown in FIG. 8 is an exemplary portion of the EGM signal obtained at step 902.

Still referring to FIG. 9, step 904 involves the IMD identifying a feature of the EGM signal indicative of a ventricular depolarization of the patient's heart. In accordance with certain embodiment, step 904 is performed by identifying a QRS complex of the EGM signal, or more specifically, an R-wave of the EGM signal. An R-wave can be detected by detecting a maximum peak of the EGM signal, or detecting an R-wave threshold crossing, but is not limited thereto.

Step 906 in FIG. 9 involves the IMD transmitting a conductive communication signal through patient tissue using at least two implanted electrodes of the IMD, wherein the conductive communication signal indicates when the ventricular depolarization of the patient's heart occurred. Referring briefly back to FIGS. 2 and 3, the electrodes 108 are examples of electrodes of an IMD that can be used to transmit conductive communication signals, such as the conductive communication signal transmitted at step 904. Electrodes of a lead of a more conventional type of pacemaker can alternatively be used to transmit the conductive communication signal, as could subQ electrodes of a subQ ICD. In certain embodiments the same electrodes that are used to sense an EGM signal are also used for transmitting the conductive communication signal that indicates when the ventricular depolarization of the patient's heart occurred. Alternatively, one or more different electrodes can be used to transmit the conductive communication signal than is/are used to sense the EGM signal.

Step 908 in FIG. 9 involves an external device (ED), worn against skin of the patient, receiving the conductive communication signal (that was transmitted at step 906) using at least two electrodes of the ED that are in contact with skin of the patient against which the ED is worn. Referring briefly back to FIGS. 6A and 6B, the body worn device 122 shown therein is an example such an ED, and the electrodes 634 are examples of electrodes of the ED that are in contact with skin of the patient against which the ED is worn.

Step 910 in FIG. 9 involves the ED (e.g., 122) sensing a plethysmography (PG) signal indicative of variations in blood volume in a region of the patient adjacent to the ED. The portion of the PG signal 812 shown in FIG. 8 is an exemplary portion of the PG signal obtained at step 910. The PG signal obtained at step 910 can be a PPG signal sensed using an optical sensor that includes one or more light emitting elements (e.g., 636), and one or more light detecting elements (e.g., 638) of an ED (e.g., 122). The PG signal obtained at step 910 can alternatively be an IPG signal sensed using electrodes (e.g., 634) of an ED (e.g., 122). In other words, the same electrodes of the ED that are used to receive the conductive communication signal at step 908, can also be used to sense an IPG signal at step 910. Alternatively, one or more different electrodes can be used to receive the conductive communication signal than is/are used to sense the IPG signal, in which case, the ED (e.g., 122) would include more than two electrodes.

Step 912 in FIG. 9 involves the ED (e.g., 122) identifying a feature of the PG signal (sensed at step 910) indicative of when a pulse wave responsive to the ventricular depolarization reaches the region of the patient adjacent to the ED. In accordance with certain embodiments, the feature of the PG signal that is identified at step 912 is the foot (i.e., minimum peak) of the PG signal. Alternative features of the PG signal that can be identified at step 912 include, but are not limited to, the maximum upward slope, the maximum amplitude, the dicrotic notch, the maximum downward slope prior to the dicrotic notch, and the maximum downward slope following the dicrotic notch.

Step 914 in FIG. 9 involves the ED determining a time delay (TD) based on the conductive communication signal received by the ED from the IMD, and based on the feature of the PG signal identified by the ED, wherein the TD (which is indicative of how long it takes the pulse wave to travel from the patient's heart to the region of the patient adjacent to the ED) is a surrogate of the patient's blood pressure and can be used to monitor the patient's blood pressure and/or changes therein. In accordance with certain embodiments, step 914 involves determining a time difference between when the conductive communication signal that was received at step 908 and the feature of the PG signal was identified at step 912. Alternatively, if the IMD and the ED are synchronized, and there is a time stamp (of when the ventricular depolarization occurred) within the conductive communication signal, step 914 can involve determine a time difference between such a time stamp and when the feature of the PG signal was identified. Other variations are also possible and within the scope of the embodiments described herein so long as the time delay determined at step 914 is indicative of how long it takes for a pulse wave to travel from the patient's heart to the region of the patient (e.g., wrist or ankle) adjacent to the ED.

Step 916 in FIG. 9 involves monitoring a patient's blood pressure and/or changes therein based on the time delay (TD) determined at step 914. Step 916 can be achieved by using an equation, look up table (LUT), or the like, to convert the value of the TD to a value of blood pressure. Further, changes in the TD are indicative of changes in blood pressure, and can be used to monitor increases and/or decreases in blood pressure whether or not the values of the TD are converted to values of blood pressure.

The total amount of time that it takes for the IMD to detect an R-wave (or other feature) at step 904, for the IMD to transmit the conductive communication signal at step 906, and the ED to detect the conductive communication signal at step 908, is on the order of less than 0.5 microseconds ($\mu$s). In other words, steps 904, 906, and 908 collectively occur almost instantaneously with the occurrence of a ventricular depolarization. By contrast, the amount of time it takes a pulse wave to travel from the patient's heart to the region of the patient (e.g., wrist or ankle) adjacent to the ED is on the order of tens of microseconds, and more specifically, is likely to be within the range of about 80 $\mu$s to 180 $\mu$s. In other words, the time delay (TD) that is determined at step 914 is at least two orders of magnitude greater than the total amount of time it takes for steps 904, 906, and 908 to be collectively performed. Accordingly, the small delay that occurs between steps 904 through 908 can be ignored, while still allowing for relatively accurate measures of blood pressure, and/or changes therein, to be tracked.

In some literature, the time that it takes for a pulse pressure waveform to propagate through an arterial tree is often referred to in the art as the pulse transmit time (PTT), but is sometimes referred to instead of the pulse arrival time (PAT). In other words, the terms PTT and PAT are sometimes used synonymously. In other literature, the terms PTT and PAT are distinguished from one another, and PAT is considered to be equal to the sum of the PTT plus the pre-ejection period. The TD that is determined at step 914 is essentially a measure of PTT. Accordingly, the known formulas that are used to convert PTT to a measure of blood pressure can be used with embodiments of the present technology to monitor blood pressure, and changes therein, based on the TD that is determined at step 914.

In accordance with certain embodiments, in order to measure the TD, the ED (e.g., 122) starts a timer when it receives the conductive communication signal (indicating when the ventricular depolarization of the patient's heart occurred), and the ED stops the timer when it detects a feature of the PG signal (indicative of when a pulse wave responsive to the ventricular depolarization reaches the region of the patient adjacent to the ED), with the value of the timer when it is stopped being the TD.

It is known that the electromagnetic propagation of the conductive signal is limited by the dielectric properties of the body, and that the velocity v can be approximated by the following equation:

$$v \approx \frac{3 \times 10^8}{\sqrt{\varepsilon}}$$

where ε is the relative permittivity of the medium.

If the human body is ideally modeled as a constant dielectric consisting of muscle (c is approximately 8000 at a frequency of 100 kHz), the velocity would be about 3.35 meters per microsecond (m/μs). If it is estimated that 1.5 meters (m) is the typical distance from a person's chest to wrist (assuming that the body worn device 122 is worn on a person's wrist), then the time for the electrical signal to travel this distance would be approximately 450 ns. It can also be approximated that it would take a similar amount of time for an electrical signal to travel from a person's chest to ankle (assuming that the body worn device 122 is worn on a person's ankle). This is for illustrative purposes, as an actual human body is not a homogenous dielectric.

The PTT (which is referred to above at the time delay (TD)) can be modeled by the Moens-Kortweg following equation:

$$PTT = \frac{L}{\sqrt{\frac{hE_0 e^{\varsigma P}}{\rho R}}}$$

where L is the length of the vessel, h is the thickness of the vessel wall, P is the blood pressure of interest, R is the radius of the vessel, ρ is the blood density, $E_0$ is the zero-pressure modulus in mmHg, and ç is a constant that depends on the vessel (typically 0.016 mmHg$^{-1}$ to 0.018 mmHg$^{-1}$). In accordance with certain embodiments of the present technology, a patient's blood pressure (P) can be determined by solving for P in the above equation. Various other equations can be used to determine a patient's blood pressure (BP) based on a value of TD or PTT. For example, the equation:

$$BP = \frac{A}{PTT^2} + B,$$

where A and B are constants. The same values for A and B can be used for an entire patient population, or more preferably, values for A and B can be selected for a specific patient during a calibration procedure. Another equation that can be used to determine a value for blood pressure (BP) is the linear approximation equation: BP=a*PTT+b, where a and b are constants. The same value a and b can be used for an entire patient population, or more preferably, values for a and b can be selected for a specific patient during a calibration procedure.

Still another equation that can be used to determine a value for blood pressure (BP) is the non-linear equation: BP=a*ln(PTT)+b, where a and b are constants, which can be the same for an entire patient population, or more preferably, can be selected for a specific patient during a calibration procedure. A further equation that can be used to determine a value for blood pressure (BP) is the equation: BP=a*PTT+b*HR+c, where a, b and c are constants, which can be the same for an entire patient population, or more preferably, can be selected for a specific patient during a calibration procedure. In this latter equation, the patient's heart rate (HR) can be determined based on one or more R-R intervals in the EGM signal, and/or one or more peak-to-peak intervals of the PG signalbut is not limited thereto. , Other equations, besides those mentioned above, can be used to convert values of PTT or TD to values of BP. Changes in blood pressure can be determined by tracking changes in the values calculated for BP. Alternatively, an equation can be used to track changes in BP. For example, a change in blood pressure (BP) can be calculated using the equation:

$$\Delta BP = \frac{2}{\gamma PTT} + \Delta PTT,$$

where γ is a coefficient ranging from 0.016 to 0.019 mmHg, which depends on the particular vessel (and can be approximated as 0.017 mmHG), and ΔPTT is the change in PTT, which can be the change in the TD. In any of the above equations, the value determined for TD can be used as the value for PTT in those equations. Other equations, besides that mentioned above, can be used to determine changes in blood pressure.

The conductive communication signal (indicating when the ventricular depolarization of the patient's heart occurred) will need to travel about 1.5 meters between the IMD that transmits the conductive communication signal and the ED that detects the conductive communication signal, which can result in about 80 dB or more of attenuation. Accordingly, if the peak to peak magnitude of the conductive communication signal is 3 volts (V), attenuation by 80 dB results in conductive communication signals (received by the ED) having a peak to peak magnitude of about 300 microvolts (μV). The ED (e.g., 122) can be designed such that it can detect such relatively low magnitude conductive communication signals. Alternatively, or additionally, the IMD (e.g., 102) can increase from time to time (e.g., periodically, or in response to some triggering event) the amplitude of the conductive communication signal that indicates when a ventricular depolarization of the patient's heart occurred, to thereby increase a probability that the ED can detect the conductive communication signal.

In accordance with certain embodiments, the IMD transmits the conductive communication signal (that indicates when a ventricular depolarization of the patient's heart occurred), using at least two implanted electrodes of the IMD, during a refractory period that follows the ventricular depolarization of the patient's heart. This will ensure that the conductive communication signal, even if transmitted at a relative high magnitude, will not cause inadvertent capture of the patient's heart.

Figure 10:
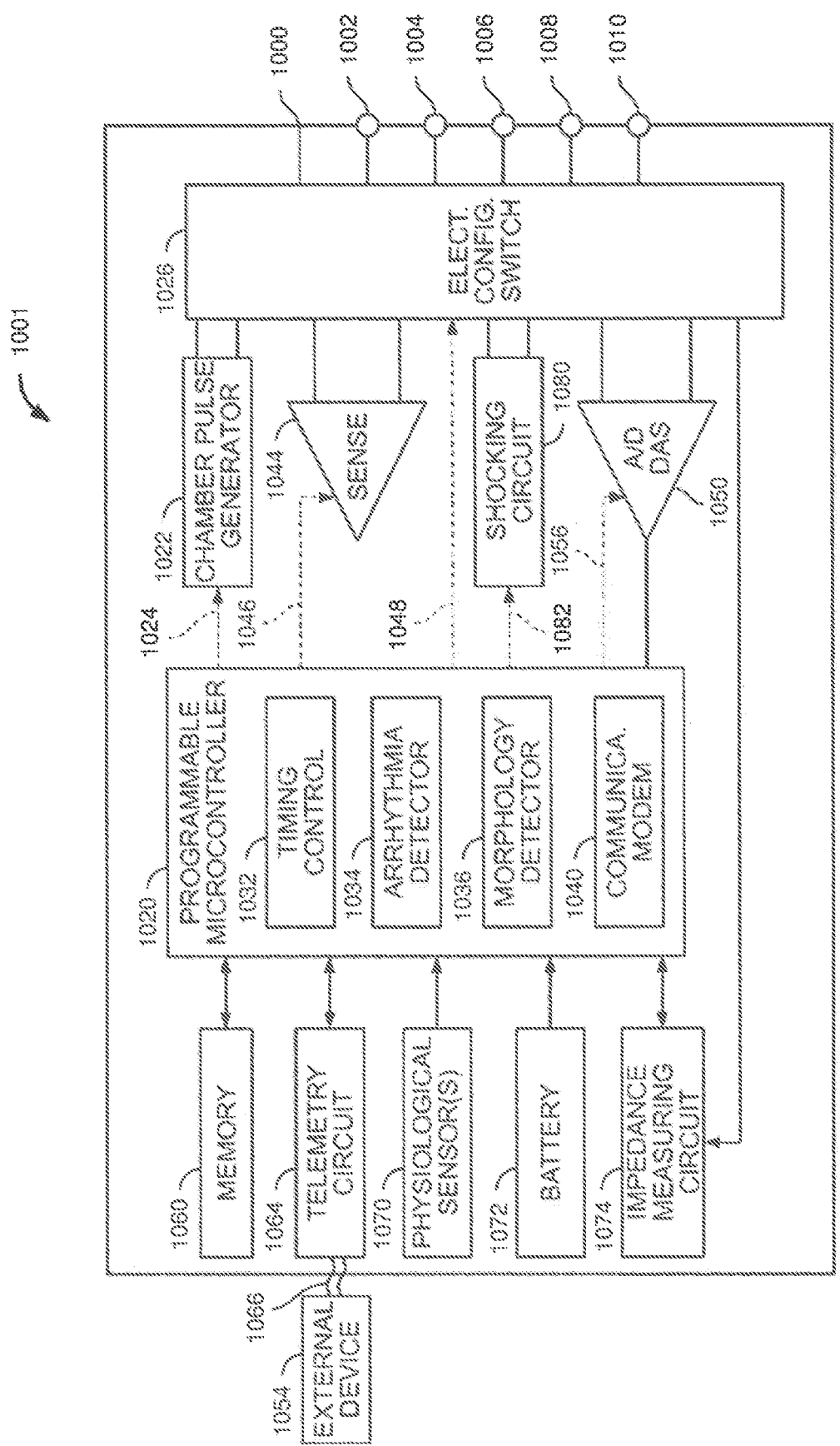
FIG. 10 shows a block diagram of one embodiment of an IMD (e.g., LP) that is implanted into the patient as part of the implantable cardiac system in accordance with certain embodiments herein.

FIG. 10 shows a block diagram of one embodiment of an IMD 1001 that is implanted into the patient as part of the implantable system in accordance with certain embodiments herein. The IMD 1001 can be an LP, such as the LP 102 discussed above, or can be some other type of IMD. The IMD 1001 may be implemented as a full-function biventricular pacemaker, equipped with both atrial and ventricular sensing and pacing circuitry for four chamber sensing and stimulation therapy (including both pacing and shock treatment). Optionally, IMD 1001 may provide full-function cardiac resynchronization therapy. Alternatively, IMD 1001 may be implemented with a reduced set of functions and components. For instance, the IMD may be implemented without ventricular sensing and pacing, and can be primarily used as a monitor.

The IMD 1001 has a housing 1000 to hold the electronic/computing components. Housing 1000 (which is often referred to as the "can", "case", "encasing", or "case electrode") may be programmably selected to act as the return electrode for certain stimulus modes. Housing 1000 may further include a connector (not shown) with a plurality of terminals 1002, 1004, 1006, 1008, and 1010. The terminals may be connected to electrodes that are located in various locations on housing 1000 or elsewhere within and about the heart. IMD 1001 includes a programmable microcontroller 1020 that controls various operations of IMD 1001, including cardiac monitoring and stimulation therapy. Microcontroller 1020 includes a microprocessor (or equivalent control circuitry), RAM and/or ROM memory, logic and timing circuitry, state machine circuitry, and I/O circuitry.

IMD 1001 further includes a first pulse generator 1022 that generates stimulation pulses for delivery by one or more electrodes coupled thereto. Pulse generator 1022 is controlled by microcontroller 1020 via control signal 1024. Pulse generator 1022 may be coupled to the select electrode(s) via an electrode configuration switch 1026, which includes multiple switches for connecting the desired electrodes to the appropriate I/O circuits, thereby facilitating electrode programmability. Switch 1026 is controlled by a control signal 1028 from microcontroller 1020.

In the embodiment of FIG. 10, a single pulse generator 1022 is illustrated. Optionally, the IMD may include multiple pulse generators, similar to pulse generator 1022, where each pulse generator is coupled to one or more electrodes and controlled by microcontroller 1020 to deliver select stimulus pulse(s) to the corresponding one or more electrodes.

Microcontroller 1020 is illustrated as including timing control circuitry 1032 to control the timing of the stimulation pulses (e.g., pacing rate, atrioventricular (AV) delay, atrial interconduction (A-A) delay, or ventricular interconduction (V-V) delay, etc.). Timing control circuitry 1032 may also be used for the timing of refractory periods, blanking intervals, noise detection windows, evoked response windows, alert intervals, marker channel timing, and so on. Microcontroller 1020 also has an arrhythmia detector 1034 for detecting arrhythmia conditions and a morphology detector 1036. Although not shown, the microcontroller 1020 may further include other dedicated circuitry and/or firmware/software components that assist in monitoring various conditions of the patient's heart and managing pacing therapies.

IMD 1001 is further equipped with a communication modem (modulator/demodulator) 1040 to enable wireless communication with the remote slave pacing unit. Modem 1040 may include one or more transmitters and two or more receivers as discussed herein in connection with FIG. 1B. In one implementation, modem 1040 may use low or high frequency modulation. As one example, modem 1040 may transmit i2i messages and other signals through conductive communication between a pair of electrodes. Modem 1040 may be implemented in hardware as part of microcontroller 1020, or as software/firmware instructions programmed into and executed by microcontroller 1020. Alternatively, modem 1040 may reside separately from the microcontroller as a standalone component.

IMD 1001 includes a sensing circuit 1044 selectively coupled to one or more electrodes, that perform sensing operations, through switch 1026 to detect the presence of cardiac activity in the right chambers of the heart. Sensing circuit 1044 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1026 determines the sensing polarity of the cardiac signal by selectively closing the appropriate switches. In this way, the clinician may program the sensing polarity independent of the stimulation polarity.

The output of sensing circuit 1044 is connected to microcontroller 1020 which, in turn, triggers or inhibits the pulse generator 1022 in response to the presence or absence of cardiac activity. Sensing circuit 1044 receives a control signal 1046 from microcontroller 1020 for purposes of controlling the gain, threshold, polarization charge removal circuitry (not shown), and the timing of any blocking circuitry (not shown) coupled to the inputs of the sensing circuitry.

In the embodiment of FIG. 10, a single sensing circuit 1044 is illustrated. Optionally, the IMD may include multiple sensing circuits, similar to sensing circuit 1044, where each sensing circuit is coupled to one or more electrodes and controlled by microcontroller 1020 to sense electrical activity detected at the corresponding one or more electrodes. Sensing circuit 1044 may operate in a unipolar sensing configuration or in a bipolar sensing configuration.

IMD 1001 further includes an analog-to-digital (A/D) data acquisition system (DAS) 1050 coupled to one or more electrodes via switch 1026 to sample cardiac signals across any pair of desired electrodes. Data acquisition system 1050 is configured to acquire intracardiac electrogram signals, convert the raw analog data into digital data, and store the digital data for later processing and/or telemetric transmission to an external device 1054 (e.g., a programmer, local transceiver, or a diagnostic system analyzer). Data acquisition system 1050 is controlled by a control signal 1056 from the microcontroller 1020.

Microcontroller 1020 is coupled to a memory 1060 by a suitable data/address bus. The programmable operating parameters used by microcontroller 1020 are stored in memory 1060 and used to customize the operation of IMD 1001 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of IMD 1001 may be non-invasively programmed into memory 1060 through a telemetry circuit 1064 in telemetric communication via communication link 1066 with external device 1054. Telemetry circuit 1064 allows intracardiac electrograms and status information relating to the operation of IMD 1001 (as contained in microcontroller 1020 or memory 1060) to be sent to external device 1054 through communication link 1066.

IMD 1001 can further include magnet detection circuitry (not shown), coupled to microcontroller 1020, to detect when a magnet is placed over the unit. A magnet may be used by a clinician to perform various test functions of IMD 1001 and/or to signal microcontroller 1020 that external device 1054 is in place to receive or transmit data to microcontroller 1020 through telemetry circuits 1064.

IMD 1001 can further include one or more physiological sensors 1070. Such sensors are commonly referred to as "rate-responsive" sensors because they are typically used to adjust pacing stimulation rates according to the exercise state of the patient. However, physiological sensor 1070 may further be used to detect changes in cardiac output, changes in the physiological condition of the heart, or diurnal changes in activity (e.g., detecting sleep and wake states). Signals generated by physiological sensors 1070 are passed to microcontroller 1020 for analysis. Microcontroller 1020 responds by adjusting the various pacing parameters (such as rate, AV Delay, V-V Delay, etc.) at which the atrial and ventricular pacing pulses are administered. While shown as being included within IMD 1001, physiological sensor(s) 1070 may be external to IMD 1001, yet still be implanted within or carried by the patient. Examples of physiologic sensors might include sensors that, for example, sense respiration rate, pH of blood, ventricular gradient, activity, position/posture, minute ventilation (MV), and so forth.

A battery 1072 provides operating power to all of the components in IMD 1001. Battery 1072 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1072 also desirably has a predictable discharge characteristic so that elective replacement time can be detected. As one example, IMD 1001 employs lithium/silver vanadium oxide batteries.

IMD 1001 further includes an impedance measuring circuit 1074, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1074 is coupled to switch 1026 so that any desired electrode may be used. In this embodiment IMD 1001 further includes a shocking circuit 1080 coupled to microcontroller 1020 by a data/address bus 1082.

As noted above, the IMD 1001 can be an LP 102. In some embodiments, the LPs 102*a* and 102*b* are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology can also be used with other types of IMDs besides an LP. Accordingly, unless specifically limited to use with an LP, the claims should not be limited to use with LP type IMDs.

In the above description, the TD (using to monitor blood pressure) was often described as being the time between the occurrence of a QRS complex or R-wave and when a specific feature of a PG signal (PPG or IPG signal) is detected at a periphery of the patient. A QRS complex and R-wave are indicative of an intrinsic ventricular depolarization. In accordance with alternative embodiments, the TD (using to monitor blood pressure) can instead be determined by determining the time between when a ventricular pacing pulse is delivered (which causes a paced ventricular depolarization) and when a specific feature of a PG signal (PPG or IPG signal) is detected at a periphery of the patient. In such embodiments, the pacing pulse (that is used to cause the paced ventricular depolarization) can be encoded with an indication that a ventricular depolarization occurred (because it was caused). Accordingly, a conductive communication signal that an IMD transmits through patient tissue using at least two implanted electrodes of the IMD, and which informs the body worn device 122 when a ventricular depolarization of the patient's heart occurred, may indicate that a paced ventricular depolarization occurred. For example, such a conductive communication signal can include a VP marker, which as noted above in Table 2, provides for the notification of a paced event in a ventricle.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use in monitoring a patient's blood pressure, the method comprising:
   (a) an implantable medical device (IMD) sensing an electrogram (EGM) signal indicative of cardiac electrical activity of the patient's heart;
   (b) the IMD identifying a feature of the EGM signal indicative of a ventricular depolarization of the patient's heart;
   (c) the IMD transmitting a conductive communication signal through patient tissue using at least two implanted electrodes of the IMD, the conductive communication signal indicating when the ventricular depolarization of the patient's heart occurred;
   (d) an external device (ED), worn against skin of the patient, receiving the conductive communication signal using at least two electrodes of the ED that are in contact with skin of the patient against which the ED is worn, and in response thereto the ED starting a timer of the ED;
   (e) the external device (ED) sensing a plethysmography (PG) signal indicative of variations in blood volume in a region of the patient adjacent to the ED;
   (f) the ED identifying a feature of the PG signal indicative of when a pulse wave responsive to the ventricular depolarization reaches the region of the patient adjacent to the ED, and in response thereto the ED stopping the timer of the ED; and
   (g) the ED determining a time delay (TD) based on the timer that is started in response to the ED receiving the conductive communication signal indicating when the ventricular depolarization of the patient's heart occurred, and that is stopped in response to the ED identifying the feature of the PG signal indicative of when the pulse wave responsive to the ventricular depolarization reached the region of the patient adjacent to the ED;
   wherein the TD, which is indicative of how long it takes the pulse wave to travel from the patient's heart to the region of the patient adjacent to the ED, is a surrogate of the patient's blood pressure and can be used to monitor the patient's blood pressure and/or changes therein.

2. The method of claim 1, further comprising:
   (h) the ED monitoring the patient's blood pressure and/or changes therein based on the TD.

3. The method of claim 1, wherein the IMD comprises a leadless pacemaker (LP) that is implanted in or on a cardiac chamber of the patient's heart.

4. The method of claim 1, wherein the IMD is a first IMD configured to transmit conductive communication signals through patient tissue to a second IMD, with at least some of the conductive communication signals transmitted from the first IMD to the second IMD indicating when a ventricular depolarization of the patient's heart occurred, the method further comprising:
   the first IMD periodically increasing an amplitude of a said conductive communication signal indicating when a ventricular depolarization of the patient's heart occurred, to thereby periodically increase a probability that the ED can detect the said conductive communication signal.

5. The method of claim 1, wherein a same two implanted electrodes of the IMD that are used to perform the sensing the EGM are also used to perform the transmitting the conductive communication signal through patient tissue.

6. The method of claim 1, wherein the IMD transmits the conductive communication signal through patient tissue, using at least two implanted electrodes of the IMD, during a refractory period that follows the ventricular depolarization of the patient's heart.

7. The method of claim 1, wherein the ED comprises a wrist worn device.

8. The method of claim 1, wherein PG signal comprises a photoplethysmography (PPG) signal and a sensor of the ED that senses the PPG signal comprises an optical sensor that includes at least one light emitting element and at least one light detecting element.

9. The method of claim 1, wherein the PG signal comprises an impedance plethysmography (IPG) signal and a sensor of the ED that senses the IPG signal comprises at least two electrodes.

10. The method of claim 9, wherein a same two electrodes of the ED that are used to receive the conductive communication signal are also used to sense the IPG signal.

11. A system for use in monitoring a patient's blood pressure, the system comprising:
    an implantable medical device (IMD) comprising two or more implantable electrodes, the IMD configured to
       sense an electrogram (EGM) signal using at least two of the two or more implantable electrodes of the IMD, the EGM signal indicative of cardiac electrical activity of the patient's heart;
       identify a feature of the EGM signal indicative of a ventricular depolarization of the patient's heart; and
       transmit a conductive communication signal through patient tissue using at least two of the two or more implantable electrodes of the IMD, the conductive communication signal indicating when the ventricular depolarization of the patient's heart occurred; and
    an external device (ED) comprising two or more external electrodes and a timer, the ED configured to be worn against skin of a patient such that at least two of the two or more external electrodes are in contact with the skin of the patient, the ED further configured to
       receive the conductive communication signal indicating when the ventricular depolarization of the patient's heart occurred, using at least two of the two or more external electrodes of the ED that are in contact with skin of the patient against which the ED is worn;
       start the timer in response the conductive communication signal, indicating when the ventricular depolarization of the patient's heart occurred, being received;
       sense a plethysmography (PG) signal indicative of variations in blood volume in a region of the patient adjacent to the ED;

identify a feature of the PG signal indicative of when a pulse wave responsive to the ventricular depolarization reaches the region of the patient adjacent to the ED;

stop the timer in response to the feature of the PG signal, indicative of when the pulse wave responsive to the ventricular depolarization reached the region of the patient adjacent to the ED, being identified; and determine a delay time (TD) based on the timer that is started in response to the conductive communication signal indicating when the ventricular depolarization of the patient's heart occurred being received, and that is stopped in response to the feature of the PG signal indicative of when the pulse wave responsive to the ventricular depolarization reached the region of the patient adjacent to the ED being identified;

wherein the TD, which is indicative of how long it takes the pulse wave to travel from the patient's heart to the region of the patient adjacent to the ED, is a surrogate of the patient's blood pressure and can be used to monitor the patient's blood pressure and/or changes therein.

12. The system of claim 11, wherein the ED is further configured to monitor the patient's blood pressure and/or changes therein based on the TD.

13. The system of claim 11, wherein the IMD comprises a leadless pacemaker (LP) that is configured to implanted in or on a cardiac chamber of a patient's heart.

14. The system of claim 11, wherein the IMD is a first IMD and is configured to:

transmit conductive communication signals through patient tissue to a second IMD, with at least some of the conductive communication signals transmitted from the first IMD to the second IMD indicating when a ventricular depolarization of the patient's heart occurred; and periodically increase an amplitude of a said conductive communication signal indicating when a ventricular depolarization of the patient's heart occurred, to thereby periodically increase a probability that the ED can detect the said conductive communication signal.

15. The system of claim 11, wherein a same two implantable electrodes of the IMD that are used to sense the EGM are also used to transmit the conductive communication signal, receivable by the ED, through patient tissue.

16. The system of claim 11, wherein the IMD is configured to transmit the conductive communication signal through patient tissue, using the at least two of the two or more implantable electrodes of the IMD, indicating when the ventricular depolarization of the patient's heart occurred, during a refractory period that follows the ventricular depolarization of the patient's heart.

17. The system of claim 11, wherein the ED comprises a wrist worn device.

18. The system of claim 11, wherein PG signal comprises a photoplethysmography (PPG) signal and a sensor of the ED that senses the PPG signal comprises an optical sensor that includes at least one light emitting element and at least one light detecting element.

19. The system of claim 11, wherein the PG signal comprises an impedance plethysmography (IPG) signal and a sensor of the ED that senses the IPG signal comprises at least two of the two or more external electrodes of the ED.

20. The system of claim 19, wherein a same two external electrodes of the ED that are used to receive the conductive communication signal are also used to sense the IPG signal.

21. A device configured to be worn on a patient's body, the device comprising:

a two or more electrodes configured to be in contact with skin of the patient wearing the device;

a timer;

a receiver coupled to at least two of the two or more electrodes and configured to receive a conductive communication signal from an implantable medical device (IMD), using at least two of the two or more electrodes that are in contact with skin of the patient wearing the device, the conductive communication signal indicating when a ventricular depolarization of the patient's heart occurred;

a sensor configured to sense a plethysmography (PG) signal indicative of variations in blood volume in a region of the patient adjacent to the device;

one or more processors configured to start the timer in response to the conductive communication signal, indicating when the ventricular depolarization of the patient's heart occurred, being received by the receiver;

identify a feature of the PG signal indicative of when a pulse wave responsive to the ventricular depolarization reaches the region of the patient adjacent to the device;

stop the timer in response to the feature of the PG signal, indicative of when the pulse wave responsive to the ventricular depolarization reaches the region of the patient adjacent to the device, being identified; and determine a delay time (TD) based on the timer that is started in response to the receiver receiving the conductive communication signal indicating when the ventricular depolarization of the patient's heart occurred, and that is stopped in response to the feature of the PG signal indicative of when the pulse wave responsive to the ventricular depolarization reached the region of the patient adjacent to the device being identified, wherein the TD is indicative of how long it takes a pulse wave to travel from the patient's heart to the region of the patient adjacent to the device; and monitor the patient's blood pressure, and/or changes therein, based on the TD.

22. The device of claim 21, further comprising a strap that is configured to attach the device to a patient's arm, wrist or ankle.

23. The device of claim 21, wherein the device comprises a patch that is configured to be adhered to a patient's body.

24. The device of claim 21, wherein PG signal comprises a photoplethysmography (PPG) signal and the sensor that senses the PPG signal comprises an optical sensor that includes at least one light emitting element and at least one light detecting element.

25. The device of claim 21, wherein PG signal comprises an impedance plethysmography (IPG) signal and a sensor that senses the IPG signal comprises at least two electrodes.

26. The device of claim 25, wherein a same two electrodes of the device that are used to receive the conductive communication signal are also used to sense the IPG signal.

\* \* \* \* \*